(12) United States Patent
Kim et al.

(10) Patent No.: US 11,207,389 B2
(45) Date of Patent: Dec. 28, 2021

(54) COMPOSITION FOR TREATMENT OR PREVENTION OF INFECTIOUS INFLAMMATORY DISEASES, OR COMPOSITION FOR IMMUNE ENHANCEMENT, COMPRISING TRYPTOPHANYL-TRNA SYNTHETASE AS AN ACTIVE INGREDIENT

(71) Applicant: MirimGENE CO., LTD., Incheon (KR)

(72) Inventors: Sunghoon Kim, Seoul (KR); Mi Rim Jin, Seoul (KR); Young Ha Ahn, Daejeon (KR)

(73) Assignee: MIRIMGENE CO., LTD., Incheon (KR)

( * ) Notice: Subject to any disclaimer, the term of this patent is extended or adjusted under 35 U.S.C. 154(b) by 530 days.

(21) Appl. No.: 15/686,557

(22) Filed: Aug. 25, 2017

(65) Prior Publication Data
US 2018/0064790 A1 Mar. 8, 2018

Related U.S. Application Data

(63) Continuation-in-part of application No. PCT/KR2016/001944, filed on Feb. 26, 2016.

(30) Foreign Application Priority Data

Feb. 26, 2015 (KR) .................. 10-2015-0027617

(51) Int. Cl.
| | |
|---|---|
| A61K 38/53 | (2006.01) |
| C12N 9/00 | (2006.01) |
| A61P 29/00 | (2006.01) |
| A61P 31/04 | (2006.01) |
| A61P 31/00 | (2006.01) |
| A61P 31/10 | (2006.01) |
| A61P 31/12 | (2006.01) |
| A23L 33/10 | (2016.01) |
| A23L 33/00 | (2016.01) |

(52) U.S. Cl.
CPC .............. *A61K 38/53* (2013.01); *A23L 33/10* (2016.08); *A23L 33/40* (2016.08); *A61P 29/00* (2018.01); *A61P 31/00* (2018.01); *A61P 31/04* (2018.01); *A61P 31/10* (2018.01); *A61P 31/12* (2018.01); *C12N 9/00* (2013.01); *C12Y 601/01002* (2013.01); *A23V 2002/00* (2013.01)

(58) Field of Classification Search
CPC .......... A23L 33/10; A23L 33/40; A61P 31/12; A61P 31/04; A61P 31/00; A61P 31/10; A61P 29/00; C12N 9/00; C12Y 601/01002; A61K 38/53; A23V 2002/00
See application file for complete search history.

(56) References Cited

U.S. PATENT DOCUMENTS

| | | |
|---|---|---|
| 8,404,242 B2 | 3/2013 | Zhou |
| 2013/0230508 A1 | 9/2013 | Greene |
| 2013/0273045 A1* | 10/2013 | Watkins ................ A61K 38/53 424/134.1 |
| 2013/0344096 A1 | 12/2013 | Chiang et al. |

FOREIGN PATENT DOCUMENTS

| | | | |
|---|---|---|---|
| EP | 1300468 A2 | 4/2003 | |
| WO | WO 2011072265 A1 | 6/2011 | |
| WO | WO 2011/097031 A2 | 8/2011 | |
| WO | WO-2011097031 A2 * | 8/2011 | ......... C07K 16/1045 |

OTHER PUBLICATIONS

Wakasugi et al., A human aminoacyl-tRNA synthetase as a regulator of angiogenesis, PNAS Jan. 8, 2002, vol. 99, No. 1, pp. 173-177.*
Park et al. Human lysyl-tRNA synthetase is secreted to trigger proinflammatory response. (PNAS (2005), 102(18), 6356-6361. (Year: 2005).*
Min Guo, et al., "Essential nontranslational functions of tRNA synthetases," Nature Chemical Biology, Mar. 2013, vol. 9, pp. 145-153.
Ronald A. Hitzeman, et al., "Isolation and Characterization of the Yeast 3-Phosphoglycerokinase Gene (PGK) by an Immunological Screening Technique," The Journal of Biological Chemistry, Dec. 25, 1980, vol. 255, No. 24, p. 12073-12080.
International Search Report in corresponding PCT Application No. PCT/KR2016/001944 dated May 20, 2016.

* cited by examiner

*Primary Examiner* — Sean C. Barron
(74) *Attorney, Agent, or Firm* — Leason Ellis LLP

(57) ABSTRACT

The present invention relates to a composition for treatment or prevention of infectious inflammatory diseases comprising tryptophanyl-tRNA synthetase as an active ingredient, and a composition for immune enhancement. More specifically, the present invention relates to a pharmaceutical composition for treatment or prevention of infectious inflammatory diseasess comprising tryptophanyl-tRNA synthetase as an active ingredient, a food composition for preventing or improving, a veterinary composition for preventing or treating, and a composition for immune enhancement comprising a tryptophanyl-tRNA synthetase as an active ingredient, respectively.

The composition of the present invention can be effectively used for preventing or treating diseases of humans and animals caused by infection from bacteria, viruses or fungi and the like by inhibiting infections such as bacterial, viral, and fungal infections at an early stage particularly through activating innate immune response.

5 Claims, 23 Drawing Sheets
(6 of 23 Drawing Sheet(s) Filed in Color)
Specification includes a Sequence Listing.

FIG. 8A
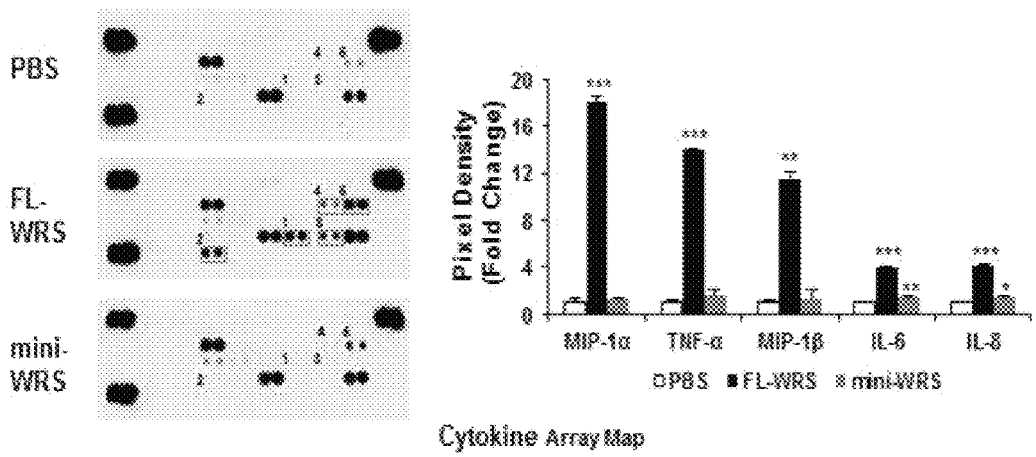
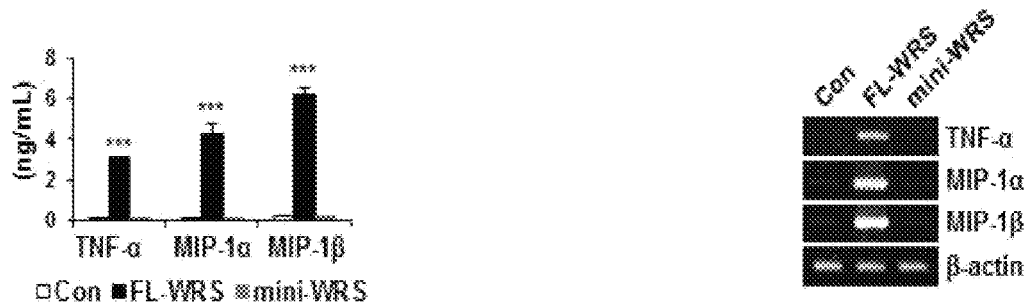
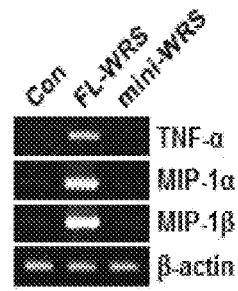
FIG. 8B
FIG. 8C

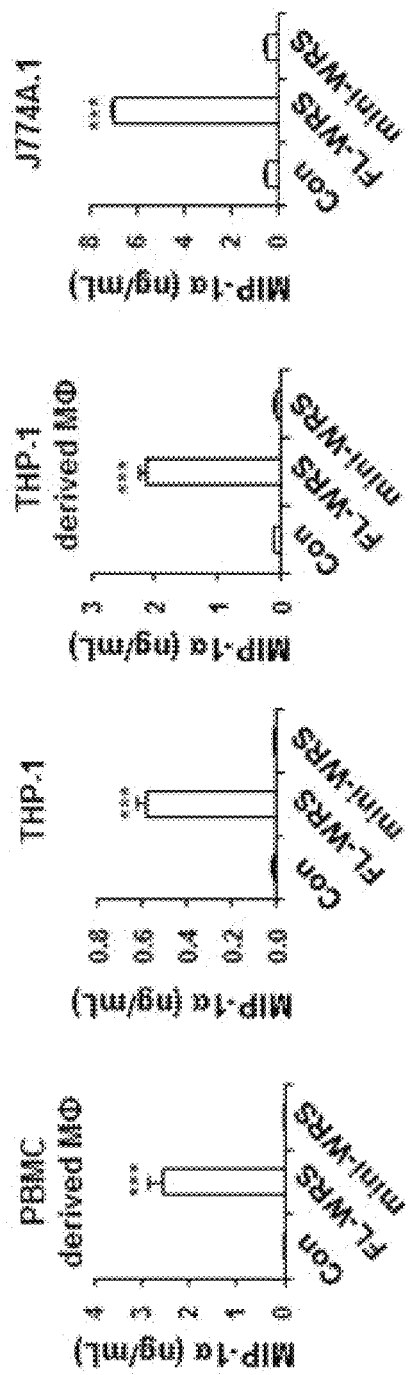
FIG. 10A
FIG. 10B
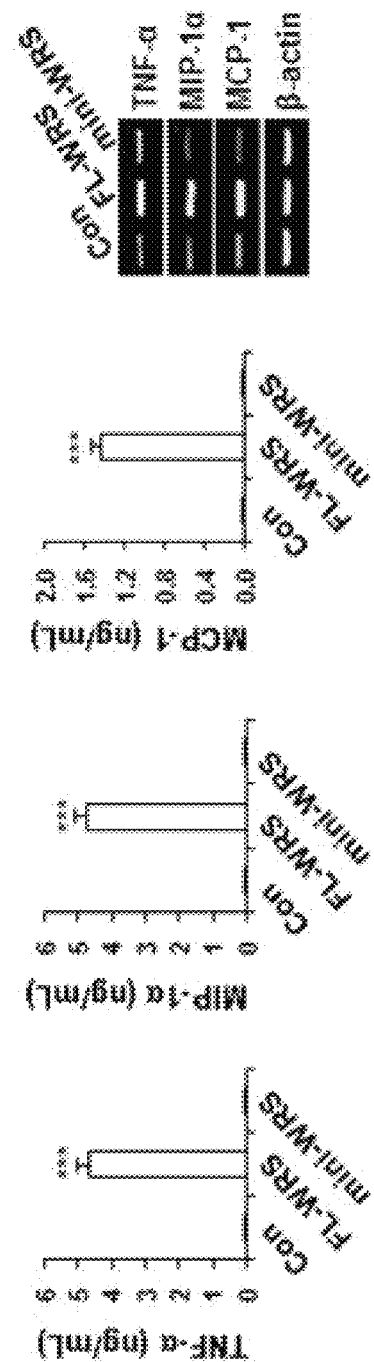
FIG. 10C

COMPOSITION FOR TREATMENT OR PREVENTION OF INFECTIOUS INFLAMMATORY DISEASES, OR COMPOSITION FOR IMMUNE ENHANCEMENT, COMPRISING TRYPTOPHANYL-TRNA SYNTHETASE AS AN ACTIVE INGREDIENT

CROSS-REFERENCE TO RELATED APPLICATIONS

The present application is a continuation-in-part of International Application No.: PCT/KR2016/001944, filed on Feb. 26, 2016, which claims priority to Korean Application No.: 10-2015-0027617, filed on Feb. 26, 2015, which are incorporated by reference in their entirety.

SEQUENCE LISTING

The instant application contains a Sequence Listing which has been submitted electronically in ASCII format and is hereby incorporated by reference in its entirety. Said ASCII copy, created on Nov. 7, 2017, is named 10524-006146-USO_SL.txt and is 36,342 bytes in size.

TECHNICAL FIELD

The present invention relates to a composition for treatment or prevention of infectious inflammatory diseases, or composition for immune enhancement, comprising tryptophanyl-tRNA synthetase (TrpRS) as an active ingredient, more particularly, the present invention relates to a pharmaceutical composition for treatment or prevention of infectious inflammatory diseases containing tryptophanyl-tRNA synthetase as an active ingredient, a food composition for prevention or improvement, a veterinary composition for treatment or prevention, and a composition for immune enhancement comprising tryptophanyl-tRNA synthetase as an active ingredient, more particularly, the present invention relates to a method for preventing, improving or treating infectious inflammatory diseases or a method for immune enhancement comprising administering an effective amount of a tryptophanyl-tRNA synthetase as an active ingredient to a subject in need thereof, and to a use for producing a therapeutic agent for preventing, improving or treating infectious inflammatory diseases or an agent for immune enhancement.

BACKGROUND TECHNOLOGY

Aminoacyl-tRNA synthetase (AARS) is an enzyme that mediates amino acid-specific binding to tRNA, and it plays a pivotal role in protein production. Recently, it is known that these AARSs are involved in various life phenomena such as apoptosis, angiogenesis, and inflammation reaction in addition to its intrinsic functions. Tryptophanyl-tRNA synthetase (TrpRS) belongings to class I of AARS and is present in the cytoplasm of a cell. It is known that mini-TrpRS, which does not contain extra N-terminal domain of TrpRS, is an angiostatic factor which is activated by IFN-γ. It is observed that full-length TrpRS was secreted in vascular cells, but it is not yet known what role it plays in the body (Guo M et al. (2013), Nat. Chem. Biol, 9 (3): 145-153).

DETAILED DESCRIPTION OF THE INVENTION

Technical Problem

While searching the novel biological functions of tryptophanyl-tRNA synthetase (TrpRS) in addition to its essential functions related with protein synthesis, the present inventors found that tryptophanyl-tRNA synthetase (TrpRS) activates innate immune responses and inhibits the infection of bacteria, fungi, viruses and the like, completing the present invention.

Accordingly, an aspect of the present invention is to provide a pharmaceutical composition for treating or preventing infectious inflammatory diseases comprising tryptophanyl-tRNA synthetase as an active ingredient.

Another aspect of the present invention is to provide a food composition for treating or preventing infectious inflammatory diseases comprising tryptophanyl-tRNA synthetase as an active ingredient.

It is still another aspect of the present invention to provide a veterinary composition for treating or preventing infectious inflammatory diseases comprising tryptophanyl-tRNA synthetase as an active ingredient.

Another aspect of the present invention is to provide a composition for immune enhancement comprising a tryptophanyl-tRNA synthetase as an active ingredient.

Another aspect of the present invention is to provide a method for preventing, ameliorating or treating infectious inflammatory diseases comprising administering to a subject in need thereof an effective amount of tryptophanyl-tRNA synthetase as an active ingredient.

Still another aspect of the present invention is to provide a use for the preparation of an agent for preventing, ameliorating or treating infectious inflammatory diseases comprising as a tryptophanyl-tRNA synthetase an active ingredient.

Still another aspect of the present invention is to provide a method for immune enhancement comprising administering to a subject in need thereof an effective amount of tryptophanyl-tRNA synthetase as an active ingredient.

Still another aspect of the present invention is to provide a use for producing an agent for immune enhancement comprising a tryptophanyl-tRNA synthetase as an active ingredient.

Technical Solution

An embodiment of the present invention is to provide a pharmaceutical composition for treating or preventing infectious inflammatory diseases comprising tryptophanyl-tRNA synthetase as an active ingredient.

Another embodiment of the present invention is to provide a food composition for preventing or ameliorating infectious inflammatory diseases comprising tryptophanyl-tRNA synthetase as an active ingredient.

Another embodiment of the present invention is to provide a veterinary composition for the prophylaxis or treatment of infectious inflammatory diseases comprising tryptophanyl-tRNA synthetase as an active ingredient.

Another embodiment of present invention is to provide a composition for immune enhancement comprising tryptophanyl tRNA synthetase as an active ingredient.

Another embodiment of present invention is to provide a method for preventing, ameliorating or treating infectious inflammatory diseases comprising administering to a subject in need thereof an effective amount of tryptophanyl-tRNA synthetase as an active ingredient.

Another embodiment of present invention is to provide a use for preparing an agent for preventing, ameliorating or treating infectious inflammatory diseases comprising tryptophanyl-tRNA synthetase as an active ingredient.

Another embodiment of present invention is to provide a method for immune enhancement comprising administering to a subject in need thereof an effective amount of tryptophanyl-tRNA synthetase as an active ingredient.

Another embodiment of present invention is to provide a use for preparing an agent for immune enhancement containing tryptophanyl-tRNA synthetase as an active ingredient.

Hereinafter, the present invention will be described in detail.

The present invention provides a pharmaceutical composition for treating or preventing infectious inflammatory diseases comprising tryptophanyl-tRNA synthetase as an active ingredient.

The tryptophanyl-tRNA synthetase may be represented by any one of the amino acid sequences selected from the group consisting of SEQ ID NO: 1 to SEQ ID NO: 8.

The inventors first discovered and disclosed herein that TrpRS has the function of inhibiting infections such as bacterial, viral and fungal infections by activating the immune system, particularly innate immune responses.

Specifically, one following Example shows that TrpRS was secreted outside the cells from the beginning of infection, when peripheral blood mononuclear cells are infected with bacteria and viruses, and secreted TrpRS increases the production of TNF-α, an inflammatory cytokine. Another Example shows that when peripheral blood mononuclear cells are infected with bacteria, TrpRS is actively secreted rather than secretion due to pyroptosis, and TrpRS, which is already present in the cell, is secreted without induction of its gene expression.

Another Example shows that TrpRS increased the secretion of various cytokines, particularly in monocytes and macrophages, and promotes macrophage differentiation and activation of their phagocystic function.

In still another Example, it is shown that the action of TrpRS increased the cell fluidity of neutrophils and monocytes, and when TrpRS is injected into the body, it induces intraperitoneal neutrophil concentration, increases the number of neutrophils and macrophages, and promote their activation.

Still another Example shows that the secretion of TNF-α and MIP-1α was decreased and the mortality rate was increased when a TrpRS-specific antibody was treated with a bacterial-infected cell to inhibit the activity of TrpRS.

Further, in another Example, when TrpRS was administered to a living body, the number of neutrophils in the abdominal cavity was increased, and it was confirmed that the bacteria were removed from the liver and spleen. This confirms that TrpRS promotes the action of removing the infecting bacteria from the body and remarkably reduces the mortality rate associated with infection.

Therefore, the present inventors discovered and disclosed herein that the tryptophan tRNA synthetase (TrpRS) of the present invention is secreted to the outside of the cell by infections such as bacterial, viral and fungal infection and TrpRS activates immune cells and is effective in the treatment or prevention of infectious inflammatory diseases.

As used herein, TrpRS or TrpRS polypeptide" refers to a polypeptide known as tryptophanyl-tRNA synthetase (TrpRS or WRS). The TrpRS polypeptide may be a polypeptide having any one of the amino acid sequences selected from the group consisting of SEQ ID NO: 1 to SEQ ID NO: 8. The TrpRS of the present invention also includes functional equivalents thereof. "Polypeptide" is used interchangeably with "polypeptides" or "protein(s)" and refers to a polymer of amino acid residues, as is commonly found in natural state proteins.

The above mentioned functional equivalent means a sequence homology (i.e., identity) of at least 70% or more, preferably 80% or more, and more preferably 90% or more with any one of amino acid sequences selected from the group consisting of SEQ ID NO: 1 to SEQ ID NO: 8. For example, a polypeptide having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of a sequence homology, which has a substantially homogenous physiological activity as a polypeptide represented by any one of amino acid sequences selected from the group consisting of SEQ ID NO: 1 to SEQ ID NO: 8. Herein, the "substantially homogenous physiological activity" means the activation of immune cell functions such as cytokine production and secretion, cell fluidity and phagocytosis of macrophage, induction of neutrophil concentration in the body, and enhancement of the action of removing the infecting bacteria.

The functional equivalents may result from the addition, substitution or deletion of an amino acid in any part of any one of the amino acid sequences selected from the group consisting of SEQ ID NO: 1 to SEQ ID NO: 8. The substitution of the amino acid is preferably a conservative substitution. Examples of conservative substitutions of amino acids present in nature are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). Also the functional equivalents include variants in which some of the amino acids are deleted in the amino acid sequence of the TrpRS polypeptide of the present invention. The deletion or substitution of the amino acid is preferably located in a region that is not directly related to the physiological activity of the polypeptide of the present invention. The deletion of the amino acid is also preferably located at a site that is not directly involved in the physiological activity of the TrpRS polypeptide. Also variants in which several amino acids have been added at both ends or sequences of the amino acid sequence of the TrpRS polypeptide are included. Also polypeptide derivatives in which some of the chemical structures of the polypeptides are modified while maintaining the basic skeleton of the polypeptide according to the present invention and its physiological activity are included within the scope of functional equivalents of the present invention. This includes, for example, structural modifications to alter the stability, shelf stability, volatility, or solubility of the polypeptides of the present invention.

In the present specification, sequence homology and homogeneity are defined as the percentage of amino acid residues in the candidate sequence to the amino acid sequence of TrpRS after aligning the candidate sequence with the amino acid sequence of TrpRS (any one of the amino acid sequences selected from the group consisting of SEQ ID NO: 1 to SEQ ID NO: 8), and introducing gaps. If necessary, conservative substitutions as a part of sequence homology are not considered to obtain maximum percent sequence homology. In addition, the stretch, deletion, or insertion of N-terminus, C-terminus, or internal region in the amino acid sequence of TrpRS is not interpreted as a sequence that affects sequence homology or homology. In addition, such homology can be determined by standard methods used to compare similar portions of amino acid sequences of two polypeptides. BLAST or similar computer program aligns two polypeptides so that each amino acid is optimally matched (along the full length sequence of one or two sequences or along the predicted portion of one or two sequences). The program provides a PAM 250 (Standard Scoring Matrix; Dayhoff et al., in Atlas of Protein Sequence and Structure, vol 5, supp 3, 1978), which provides a default opening penalty and default gap penalty and can be used in conjunction with a computer program. For example, percentage homogeneity can be calculated by multiplying the total number of identical matches by 100 and then dividing by the sum of the number of gaps introduced into the longer sequence to align two sequences with the length of the longer sequence in the matched span.

Polypeptides according to the present invention can be extracted naturally or constructed by genetic engineering methods. The nucleic acid can be constructed by PCR amplification using appropriate primers. Alternatively, DNA sequences may be synthesized by standard methods known in the art, for example, using an automated DNA synthesizer (commercially available from Biosearch or Applied Biosystems). The constructed nucleic acid is inserted into a vector comprising one or more expression control sequences (e.g., promoters, enhancers, etc.) operatively linked to the expression of the nucleic acid, and a host cell is transformed with the recombinant expression vector formed therefrom. The resulting transformant is cultured under the conditions suitable for expression of the nucleic acid, and the substantially pure polypeptide expressed by the nucleic acid is recovered from the culture. The recovery can be carried out using methods known in the art (for example, chromatography). As used herein, "substantially pure polypeptide" means that the polypeptide according to the invention is substantially free of any other proteins derived from the host cell. Genetic engineering methods for the synthesis of polypeptides of the present invention can be found in the following references: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y., Second (1998) and Third (2000) Editions; Gene Expression Technology, Method in Enzymology, Genetics and Molecular Biology, Method in Enzymology, Guthrie & Fink (eds.), Academic Press, San Diego, Calif., 1991; 및 Hitzeman et al., J. Biol. Chem., 255:12073-12080, 1990.

In addition, the polypeptides of the present invention can be readily prepared by chemical synthesis known in the art (Creighton, Proteins, Structures and Molecular Principles, W. H. Freeman and Co., NY, 1983). Representative methods include, but are not limited to, liquid or solid phase synthesis, fractional condensation, F-MOC or T-BOC chemistry (Chemical Approaches to the Synthesis of Peptides and Proteins, Williams et al., Eds., CRC Press, Boca Raton Fla., 1997; A Practical Approach, Athert on & Sheppard, Eds., IRL Press, Oxford, England, 1989).

The tryptophanyl-tRNA synthetase of the composition according to the present invention can be used in its own form or in the form of a salt, preferably a pharmaceutically acceptable salt. As used herein, the term "pharmaceutically acceptable" means physiologically acceptable and does not usually cause an allergic reaction or the like when administered to humans and the salt is preferably an acid addition salt formed by a pharmaceutically acceptable free acid. As the free acid, an organic acid and an inorganic acid can be used. The organic acids include, but are not limited to, citric, acetic, lactic, tartaric, maleic, fumaric, formic, propionic, oxalic, trifluoroacetic, benzoic, gluconic, methosulfonic, glycolic, succinic, Glutamic acid and aspartic acid. The inorganic acid includes, but is not limited to, hydrochloric acid, bromic acid, sulfuric acid, and phosphoric acid.

"Pharmacologically acceptable" refers to a nontoxic composition that is physiologically acceptable and does not inhibit the action of the active ingredient when administered to humans and does not normally cause an allergic reaction such as gastrointestinal disorder, dizziness, or the like. The pharmaceutical composition of the present invention can be formulated into various forms according to the route of administration by a method known in the art together with a pharmaceutically acceptable carrier for the immuno-stimulatory effect of tryptophanyl-tRNA synthetase. Such carriers include all kinds of solvents, dispersion media, oil-in-water or water-in-oil emulsions, aqueous compositions, liposomes, microbeads and microsomes.

The route of administration may be oral or parenteral. Parenteral administration methods include, but are not limited to, intravenous, intramuscular, intraarterial, intramedullary, intrathecal, intracardiac, transdermal, subcutaneous, intraperitoneal, intranasal, enteral, topical, sublingual or rectal administration can be.

When the pharmaceutical composition of the present invention is orally administered, the pharmaceutical composition of the present invention may be formulated into a powder, a granule, a tablet, a pill, a sugar tablet, a capsule, a liquid, a gel, a syrup, a suspension, a wafer, and the like. Examples of suitable carriers include saccharides including lactose, dextrose, sucrose, sorbitol, mannitol, xylitol, erythritol and maltitol, and starches including corn starch, wheat starch, rice starch and potato starch, and cellulose including methyl cellulose, sodium carboxymethyl cellulose and hydroxypropylmethyl cellulose, and fillers such as gelatin, polyvinyl pyrrolidone and the like. In addition, cross-linked polyvinylpyrrolidone, agar, alginic acid or sodium alginate may optionally be added as a disintegrant. Further, the pharmaceutical composition may further comprise an anticoagulant, a lubricant, a wetting agent, a flavoring agent, an emulsifying agent and an antiseptic agent.

In addition, when administered parenterally, the pharmaceutical composition of the present invention may be formulated according to methods known in the art in the form of injections, transdermal drugs, and nasal inhalers together with a suitable parenteral carrier. In the case of the injections, they must be sterilized and protected from contamination of microorganisms such as bacteria and fungi. Examples of suitable carriers for injections include, but are not limited to, solvents or dispersion media containing water, ethanol, polyols (e.g., glycerol, propylene glycol and liquid polyethylene glycol, etc.), mixtures thereof and/or vegetable oils can be. More preferably, suitable carriers include, but are not limited to, Hank's solution, Ringer's solution, phosphate buffered saline (PBS) containing triethanolamine, or isotonic solutions such as sterile water for injection, 10% ethanol, 40% propylene glycol and 5% dextrose can be used. In order to protect the injection from microbial contamination, various antibacterial and antifungal agents such as parabens, chlorobutanol, phenol, sorbic acid, thimerosal and the like may be further included. In addition, the injections may in most cases also contain isotonic agents such as sugars or sodium chloride.

Examples of transdermal dosage forms include ointments, creams, lotions, gels, solutions for external use, pastes, liniments, and air rolls. The "transdermal administration" means that a pharmaceutical composition is locally administered to the skin, whereby an effective amount of the active ingredient contained in the pharmaceutical composition is delivered into the skin. For example, the pharmaceutical composition of the present invention may be prepared into a spray-type formulation, which is gently pricked with a 30-gauge thin injection needle or directly applied to the skin. These formulations are described in the literature (Remington's Pharmaceutical Science, 15th Edition, 1975, Mack Publishing Company, Easton, Pa.), which is a prescription commonly known in pharmaceutical chemistry.

In the case of inhalation dosage forms, the compounds used according to the present invention may be formulated into a pressurized pack or a pressurized pack using a suitable propellant, for example dichlorofluoromethane, trichlorofluoromethane, dichlorotetrafluoroethane, carbon dioxide or other suitable gases. It can be conveniently delivered in the form of an aerosol spray from a nebulizer. In the case of a pressurized aerosol, the dosage unit may be determined by providing a valve that delivers a metered amount. For example, gelatin capsules and cartridges for use in an inhaler or insufflator may be formulated to contain a compound and a powder mix of a suitable powder base such as lactose or starch.

As other pharmaceutically acceptable carriers, reference may be made to those described in the following references (Remington's Pharmaceutical Sciences, 19th ed., Mack Publishing Company, Easton, Pa., 1995).

The pharmaceutical composition according to the present invention may also contain one or more buffers (e.g., saline or PBS), a carbohydrate (e.g., glucose, mannose, sucrose or dextran), an antioxidant, a bacteriostat, a chelating agent (e.g., EDTA or glutathione), an adjuvant (e.g., Aluminum hydroxide), a suspending agent, a thickening agent, and/or a preservative.

In addition, the pharmaceutical composition of the present invention may be formulated using methods known in the art so as to provide rapid, sustained or delayed release of the active ingredient after administration to the mammal.

In addition, the pharmaceutical composition of the present invention may be administered in combination with a known compound having an effect of preventing or treating an immune disease or an infectious inflammatory disease.

In the inflammatory diseases caused by the bacterial infection of the present invention, the bacterium may preferably be selected one or more from the group consisting of *Acinetobacter baumannii*, *Acinetobacter calcoaceticus*, *Acinetobacter haemolyticus*, *Acinetobacter hydrophila*, *Actinobacillus actinomycetemcomitans*, *Aeromonas hydrophila*, *Alcaligenes xylosoxidans*, *Bacteroides distasonis*, *Bacteroides fragilis*, *Bacteroides melaninogenicus*, *Bacteroides ovatus*, *Bacteroides thetaiotaomicron*, *Bacteroides vulgatus*, *Bartonella henselae*, *Bordetella pertussis*, *Branhamella catarrhalis*, *Brucella melitensis*, *Brucella abortus*, *Brucella canis*, *Burkholderia cepacia*, *Burkholderia mallei*, *Burkholderia pseudomallei*, *Campylobacter coli*, *Campylobacter fetus*, *Campylobacter jejuni*, *Citrobacter diversus*, *Citrobacter freundi*, *Citrobacter koseri*, *Coxiella burnetii*, *Edwarsiella tarda*, *Ehrlichia chafeenis*, *Eikenella corrondens*, *Enterobacter aerogenes*, *Enterobacter agglomerans*, *Enterobacter cloacae*, *Escherichia coli*, *Escherichia fergusonii*, *Escherichia vulneris*, *Flavobacterium meningosepticum*, *Francisella tularensis*, *Fusobacterium* spp., *Haemophilus ducreyi*, *Haemophilus influenzae*, *Haemophilus parainfluenzae*, *Helicobacter pylori*, *Kingella kingae*, *Klebsiella oxytoca*, *Klebsiella ozaenae*, *Klebsiella pneumoniae*, *Klebsiella rhinoscleromatis*, *Legionella pneumophila*, *Listeria monocytogenes*, *Listeria ivanovii*, *Moraxella catarrhalis*, *Morganella morganii*, *Neisseria gonorrhoeae*, *Neisseria meningitides*, *Pasteurella multoclda*, *Plesiomonas shigelloides*, *Porphyromonas asaccharolytica*, *Porphyromonas gingivalis*, *Prevotella bivia*, *Prevotella buccae*, *Prevotella corporis*, *Prevotella endodontalis*, *Prevotella intermedia*, *Prevotella melaninogenica*, *Prevotella oxalis*, *Proteus mirabilis*, *Proteus myxofaclens*, *Proteus penner*, *Proteus vulgaris*, *Providencia alcalifaciens*, *Providencia rettgeri*, *ProvidenCla stuarfii*, *Pseudomonas aeruginosa*, *Pseudomonas fluorescens*, *Ricketsia prowozekii*, *Salmonella bongori*, *Salmonella enterica*, *Serratia marcescens*, *Shigella boydii*, *Shigella dysenteriae*, *Shigella flexneri*, *Shigella sonnei*, *Staphylococcus aureus*, *Staphylococcus epidermidis*, *Staphylococcus saprophyticus*, *Stenotrophomonas maltophilia*, *Streptobacillus moniliformis*, *Vibrio alginolyticus*, *Vibrio cholerae*, *Vibrio parahaemolyticus*, *Vibrio vulunificus*, *Yersinia enterocolitica*, *Yersinia pestis*, *Yersinia pseudotuberculosis*, *Mycobacterium tuberculosis* complex, *Mycobacterium leprae* and *Mycobacterium lepromatosis*, *Mycobacterium avium* complex (MAC), *Mycobacterium kansasii*, and *Mycobacterium abscessus*.

As used herein, the inflammatory diseases caused by bacterial infections include bacterial infections occurring in mammals and birds, and diseases accompanied by bacterial infections, Preferably, it may be pneumonia, otitis media, sinusitis, bronchitis, tonsillitis and mastoiditis associated with infection by *Streptococcus pneumoniae*, *Haemophilus influenzae*, *Moraxella catarrhalis*, *Staphylococcus aureus* or genus *Peptostreptococcus*; Pharyngitis, rheumatic fever and glomerulonephritis caused by infection by *Streptococcus pyogenes*, Group C and G *streptococcus*, *Clostridium diptheriae* or *Actinobacillus haemolyticum*; airway infections associated with infection by *Mycoplasma pneumoniae*, *Legionella pneumophila*, *Streptococcus pneumoniae*, *Haemophilus influenzae*, or *Chlamydia pneumoniae*; Non-complex skin and soft-tissue infections, boils, osteomyelitis and puerperal fever associated with infection by *Staphylococcus aureus*, coagulase-positive *Staphylococcus* (e.g., *S. epidermidis*, *S. hemolyticus*, etc.), *Streptococcus pyogenes*, *Streptococcus agalactiae*, *Streptococcus* group C-F (microcolony *Streptococcus*), *Viridans streptococcus*, *Corynebacterium minutissimum*, genus *Clostridium*, or *Bartonella henselae*; Uncomplexed acute urinary tract infection; urethritis and cervicitis associated with infection by *Staphylococcus saprophyticus* or genus *Enterococcus*; and sexually transmitted disease associated with infection by *Chlamydia trachomatis*, *Haemophilus ducreyi*, *Treponema pallidum*, *Ureaplasma urealyticum*, or *Neiserria gonorrheae*; toxic diseases associated with infection by *S. aureus* (food poisoning and toxic shock syndrome), groups A, B and C streptococci; ulcers associated with infection by *Helicobacter pylori*; systemic fever syndrome associated with infection by *Borrelia recurrentis*; lyme disease associated with infection by *Borrelia burgdorferi*; conjunctivitis, keratitis and dacryocystitis associated with infection by *Chlamydia trachomatis*, *Neisseria gonorrhoeae*, *S. aureus*, *S. pneumoniae*, *S. pyogenes*, *H. influenzae* or genus *Listeria*; Diffuse *Mycobacterium avium* syndrome (MAC) disease associated with infection by *Mycobacterium avium*, *Mycobacterium intracellulare*; Gastroenteritis associated with infection by *Campylobacter jejuni*; Dental infection associated with infection by *viridans streptococcus*; Persistent cough associated with infection by *Bordetella pertussis*; Gas gangrene associated with infection by *Clostridium perfringens* or the genus *Bacteroides*; and atherosclerosis accompanied by infection by *Helicobacter pylori* or *Chlamydia pneumoniae*. Bacterial infections that can be treated, prevented or ameliorated by the composition of the present invention and diseases caused by these infections are cited in J. P. Sanford et al. ("The Sanford Guide To Antimicrobial Therapy", 26th, Antimicrobial Therapy, Inc., 1996).

The inflammatory disease caused by the bacterial infection of the present invention is most preferably a disease caused by a bacterial infection of *Escherichia* genus, *Listeria* genus, *Salmonella* genus, or *Staphylococcus* genus.

The infectious inflammatory diseases caused by viruses according to the present invention may include an inflammatory disease caused by infection such as, for example, adenovirus, herpes viruses (e.g., HSV-I, HSV-II, CMV or VZV), poxviruses (e.g., variola), orthopoxviruses such as vaccinia or *molluscum contagiosum*, picornavirus (e.g., Linovirus or enterovirus), orthomycovirus (e.g., Influenza virus), paramyxovirus (e.g., 5-para-influenza virus, mumps virus), measles virus and respiratory syncytial virus (RSV), coronavirus (e.g., SARS), papovaviruses (e.g., papilloma viruses that cause genital warts, common warts or plantar warts), hepadnavirus (e.g. hepatitis B virus), flavivirus (e.g., hepatitis B virus or hepatitis C virus or Denguevirus), or retroviruses (e.g., lentiviruses such as HIV)), cytomegalovirus, and the like. Preferably, it may be an inflammatory disease caused by infection of the virus selected from the group consisting of rhinovirus, coronavirus, influenza virus, respiratory syncytial virus (RSV), adenovirus, parainfluenza virus, herpes simplex virus, cytomegalovirus, and the like, which are caused by infection of pneumonia, influenza (influenza), or viruses known to cause respiratory tract infection.

The infectious inflammatory diseases caused by fungus according to the present invention include disorders which are related to the presence of fungus in a subject. For instance, the infectious inflammatory diseases may include topical, mucosal and/or systemic fungal infections caused by, for example, *Candida albicans, Cryptococcus neoformans, Aspergillus flavus, Aspergillus fumigatus, Coccidioides, Paracoccidioides, Histoplasma* or *Blastomyces*. Other exemplary fungal associated disorders include oral thrush, vaginal candidiasis, aspergillosis, candidosis, chromomycosis, coccidioidiocycosis, cryptococococsis, entomophthoromycosis, epizootic lymphangitis, geotrichosis, histoplasmosis, mucormycosis, mycetoma, north american blastomycosis, oomycosis, paecilimycosis, penicilliosis, rhinosporidiosis, and sprotrichiosis in animals.

Specifically, the infectious inflammatory disease of the present invention may be at least one selected from the group consisting of *salmonellosis*, food poisoning, typhoid, paratyphoid, sepsis, septic shock, systemic inflammatory response syndrome (SIRS), multiple organ dysfunction syndrome (MODS), pneumonia, pulmonary tuberculosis, tuberculosis, cold, influenza, airway infection, rhinitis, nasopharyngitis, otitis media, bronchitis, lymphadenitis, mumps, adenolymphitis, cheilitis, stomatitis, arthritis, myositis, dermatitis, vasculitis, gingivitis, pericementitis, keratitis, conjunctivitis, wound infection, peritonitis, hepatitis, osteomyelitis, cellulitis, meningitis, encephalitis, brain abscess, encephalomyelitis, cerebral meningitis, osteomyelitis, nephritis, carditis, endocarditis, enteritis, gastritis, esophagitis, duodenitis, colitis, urinary tract infection, cystitis, vaginitis, cervicitis, salpingitis, infectious erythema, bacterial dysentery, abscess and ulcer, bacteremia, diarrhea, dysentery, gastritis, gastroenteritis, genitourinary abscess, open wound or wound infection, purulent inflammation, abscesses, boils, pyoderma, impetigo, folliculitis, cellulitis, wound infection after surgery, scalded skin syndrome, skin burn syndrome, thrombotic thrombocytopenia, hemolytic uremic syndrome, renal failure, pyelonephritis, glomerulonephritis, nervous system abscess, otitis media, sinusitis, pharyngitis, tonsillitis, mastoiditis, soft tissue inflammation, dental infection, dacryocystitis, pleurisy, abdominal abscess, liver abscess, cholecystitis, spleen abscess, pericarditis, myocarditis, placentitis, amniotic fluid infection, mammitis, mastitis, puerperal fever, toxic shock syndrome, lyme disease, gas gangrene, atherosclerosis, *mycobacterium avium* syndrome (MAC), enterohaemorrhagic *Escherichia coli* (EHEC) infection, enteropathogenic *Escherichia coli* (EPEC) infection, enteroinvasive *Escherichia coli* (EIEC) infection, methicillin-resistant *Staphylococcus aureus* (MRSA) infections, vancomycin-resistant *Staphylococcus aureus* (VRSA) infections and listerosis.

*Escherichia* is a gram-negative *bacillus* with eight species belonging to the Enterobacteriaceae family Although most bacteria in *Escherichia* genus has symbiotic relationship with host and are harmless to hosts, they are a major cause of urinary tract infections and cause a variety of gastrointestinal diseases. *E. coli* is the most common pathogenic bacterium of *Escherichia*. In addition, *E. fergusonii* infected open wounds or wounds, causing bacteremia and urinary tract infection, and *E. vulneris* also mainly infect wounds.

*E. coli* is further divided into 190 serotypes according to the O, H and K antigens. The pathogenic *Escherichia coli* is classified into enterotoxigenic *E. coli* (ETEC), which produces enterotoxin, enterohemorrhagic *E. coli* (EEEC), which produces verotoxin, enteroinvasive *E. coli* (EIEC), which invades epithelial cells of the intestinal mucosa and causes tissue infection, and Enteropathogenic *E. coli* (EPEC), which causes acute gastroenteritis, and enteroaggregative *E. coli* (EAggEC). Intestinal hemorrhagic *Escherichia coli* causes hemorrhage and severe abdominal pain, rarely thrombotic thrombocytopenia or hemolytic uremic syndrome, and may cause severe renal failure. This class of *Escherichia coli* infection is called hemorrhagic colitis because of the symptoms of severe hemorrhagic diarrhea. Especially *E. coli* O157: H7 is a major food poisoning causative organism. Toxic *E. coli* is a causative organism of enteritis and traveler's diarrhea, causing diarrhea with dehydration. *Escherichia coli* is a major symptom of fever and abdominal pain. It infects the epithelial cells of the large intestine mucosa and causes infection. Therefore, ulcers are formed by cell necrosis and cause diarrhea, which is a mixture of blood and mucus. Intestinal pathogenic *Escherichia coli* exhibits symptoms of vomiting, abdominal pain, diarrhea, and fever. *Escherichia coli* is an infection mainly through patients, carriers, and animal excreta, but any food contaminated with bacteria can be a causative agent due to a wide range of distribution such as livestock, people, and natural environment.

It is known that *Listeria* is a gram-positive bacterium of even and short shape, and there are 10 species of *Listeria*. Only *L. monocytogenes* and *L. ivanovii* are the pathogens, and it is known that only *L. monocytogenes* is able to infect humans.

*Listeria* is mainly transmitted through contaminated food, and may be directly transmitted from an infected animal. Listeriosis often manifests as a fever or sepsis, such as high fever, myalgia, and can cause meningitis, encephalitis, brain abscess, etc. in the central nervous system. Infection with gastrointestinal tract causes symptoms such as fever, nausea and vomiting. It is rarely seen as a local infection such as soft tissue, conjunctivitis, pleuritis, peritonitis, hepatitis, hepatic abscess, cholecystitis, spleen abscess. It can cause major infectious symptoms such as sepsis or meningitis, and peritonitis, endocarditis, and brain abscess in patients with decreased cellular immunity, organ transplant recipients undergoing immunosuppressive treatment, elderly, and pregnant women. Pregnant women cause bacteremia similar to that of influenza. Unless they are treated early, they can cause placenta, sheep, and fetal infections, leading to miscarriage or stillbirth. Healthy adults can also cause gastroenteritis.

*Salmonella* is a rod-shaped gram negative *bacillus* belonging to the Enterobacteriaceae family. *Salmonella* genus is classified into two species, *Salmonella enterica* (*S. enterica*) and *Salmonella bongori* (*S. bongori*), and *S. enterica* again divided into six subspecies. It is composed of about 2,500 serotypes again according to the combination of the bacterial antigen (O) and the flagella antigens (H), which are *salmonella* lipopolysaccharide. Many *Salmonella* serotypes, including *S. typhi, S. enteritidis, S. paratyphi, S. typhimurium*, and *S. choleraesuis*, which cause infectious diseases in humans, belong to *enterica* subspecies.

*Salmonella* infects humans and animals through various routes including contaminated food, infected animals, water, and utensils, and causes disease. *Salmonella* infection is caused by various symptoms such as food poisoning, enteritis, sepsis, bacteremia, chronic infection and local infection. Especially in humans *S. typhi* causes typhus, *S. paratyphi* causes paratyphi, *S. typhimurium, S. enteritidis*, S. *Infantis, S. heidelberg*, etc. cause gastroenteritis. *Salmonellosis* causes gastrointestinal symptoms such as fever, headache, abdominal pain, diarrhea, nausea, vomiting, and dehydration through a latent period of 12 to 36 hours. It begins with acute enterocolitis and may progress to sepsis or bacteremia, abscess, arthritis, cholecystitis, pericarditis, pneumonia, syphilis, pyelonephritis. *Salmonella* can be transmitted through any tissue of the body.

*Staphylococcus* is a gram-positive bacterium that has single, double or irregular grape arrangement. *Staphylococcus* is classified into about 40 species, and again divided into 11 groups according to the 16s ribosomal RNA (rRNA) base sequence. Among them, *S. aureus, S. epidermidis*, and *S. saprophyticus* are the main problems in clinical practice.

*S. aureus* is a major causative agent of pyogenic inflammation and has various infectious symptoms ranging from food poisoning to sepsis. It has been shown that various toxins such as coagulase and enterotoxin, which have potent toxicity to coagulate plasma. Protein A, an intracellular component of *S. aureus*, acts on complement activation, localized swelling and seizure. The symptoms of *S. aureus* infection include the skin infection, such as folliculitis, burns, infections, impetigo, post-operative wound infections, and skin lethargy syndromes, bloodstream infection, pneumonia, arthritis, acute endocarditis, myocarditis, encephalitis, meningitis, genitourinary tract, nervous system, abdominal abscess, otitis media, conjunctivitis, toxic shock syndrome. Furthermore, *S. aureus*, which is resistant to antibiotics, is particularly difficult to treat and is a trifling problem in opportunistic infections and disease management in hospitals, schools, and prisons. They are methicillin-resistant *Staphylococcus aureus* (MRSA), which is resistant to beta-lactam antibiotics such as penicillin and methicillin, vancomycin-intermediate *S. aureus* (VISA), which is resistant to the glycoprotein antibiotic vancomycin, heterogenous vancomycin-intermediate *S. aureus* (hVISA) and high-level vancomycin-resistant *S. aureus* (VRSA), and the like. *S. epidermidis*, which is another coagulase negative pathogen of *Staphylococcus* sp. causes a pathogenic infectious disease that can be infected by therapeutic instruments, and *S. saprophyticus* causes urinary tract infection.

The present invention also provides a food composition for preventing or ameliorating infectious inflammatory diseases comprising tryptophanyl-tRNA synthetase as an active ingredient. The tryptophanyl-tRNA synthetase may be any one selected from the group consisting of SEQ ID NO: 1 to SEQ ID NO: 8.

The food composition according to the present invention includes all forms of functional food, nutritional supplement, health food and food additives. These types can be prepared in various forms according to conventional methods known in the art.

For example, as a health food, the food composition itself according to the present invention can be prepared in the form of tea, juice, and drink. Also it can be eaten in granulated, encapsulated, or powdered form. In addition, the food composition according to the present invention may be prepared in the form of a composition by mixing with known substances or active ingredients known to be effective for immune enhancement or for the prevention or improvement of diseases caused by bacterial infection.

Functional foods also can be prepared by adding the food composition according to the present invention to beverages (including alcoholic beverages), fruits and processed foods (such as canned fruits, bottled fruits, jam, marmalade), fish, meat and its processed foods (e.g., ham, sausage etc), breads and noodles (e.g., udon, buckwheat noodles, ramen noodles, spaghetti, macaroni, etc.), fruit juice, various drinks, cookies, taffy, dairy products (e.g., butter, cheeses etc.), edible vegetable oils, margarine, vegetable protein, retort food, frozen food, various kinds of seasoning (e.g., soybean paste, soy sauce, sauce, etc.).

The preferable content of the food composition according to the present invention is not limited to this, but is preferably 0.01 to 50% by weight in the finally prepared food. In order to use the composition for food according to the present invention in the form of a food additive, it may be used in the form of powder or concentrate.

The present invention also provides a veterinary composition for treating or preventing inflammatory diseases caused by infection comprising tryptophanyl-tRNA synthetase as an active ingredient. The tryptophanyl-tRNA synthetase may be any one selected from the group consisting of SEQ ID NO: 1 to SEQ ID NO: 8.

In animals, *E. coli* mainly causes colibacillosis by intestinal infections in cattle, pigs, and chickens, and causes gastrointestinal disorders such as diarrhea and atrophy of calves and uterine myositis of cattle, sepsis of pigs, diarrhea, intestinal diseases, dehydration, neurological symptoms and the like.

*Salmonella* has poultry, pigs, cows, iguanas, turtles, dogs, cats, pets, livestock and wild animals as a hospital. *Salmonellosis* in animals is an acute or chronic digestive infectious disease of livestock, mainly in cattle and swine. It often occurs in calves and is characterized by fever, enteritis, and sepsis. It can cause pneumonia, encephalitis, arthritis, and mastitis. The *salmonellosis* in pigs are often called pig paratyphoids because they cause symptoms such as gastroenteritis sepsis in the frying period. *S. gallinarum*, a serotype of *Salmonella*, causes fowl typhoid in chickens resulting in high mortality from sepsis.

In animals, *Listeria* infects a variety of livestock and wildlife, including chickens, cows, pigs, dogs, raccoons, goats, sheep, and mice. Listeriosis mainly causes abortion, sepsis, meningitis, encephalitis, etc. in ruminant animals, and it is also referred to as a circulatory disease, in which the bacterium invades the brain tissue and causes damage to the nerve cells, such as circling movement or rushing into obstacles. *Staphylococcus* is one of the common causative bacteria for bacterial infections in animals. It induces purulent diseases such as inflammation of the skin and soft tissues, and mastitis in ruminants such as cattle, sheep and goats.

The veterinary compositions of the present invention may further comprise suitable excipients and diluents according to conventional methods. Excipients and diluents that may be included in the veterinary composition include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, cetanol, stearyl alcohol, liquid paraffin, sorbitan monostearate, poly Sorbate 60, methylparaben, propylparaben, and mineral oil.

The veterinary composition of the present invention may further comprise fillers, anti-coagulants, lubricants, wetting agents, spices, emulsifiers, preservatives, and the like. The veterinary composition according to the present invention can be formulated using methods well known in the art so as to provide rapid, sustained or delayed release of the active ingredient after administration to the animal. And the formulations may be in the form of powders, granules, tablets, capsules, suspensions, emulsions, solutions, syrups, aerosols, soft or hard gelatine capsules, suppositories, sterile injectable solutions, sterile external preparations and the like.

The veterinary composition according to the present invention may vary depending on the type of animal, age, sex, and body weight, but may be administered in an amount of 0.1 to 100 mg/kg once or several times a day. The dose may also be increased or decreased depending on the route of administration, degree of disease, sex, weight, age, and the like. Accordingly, the dose does not in any way limit the scope of the invention.

The present invention also provides a composition for immune enhancement comprising tryptophanyl tRNA synthetase as an active ingredient. The tryptophanyl-tRNA synthetase may be any one selected from the group consisting of SEQ ID NO: 1 to SEQ ID NO: 8.

Immune enhancement means increasing the immune response or activity of the in vivo immune system. The composition of the present invention is effective for alleviating the immune function deterioration due to aging, pregnancy, immunosuppressive treatment or the like, or for preventing and improving diseases caused by immune dysfunction. The disease caused by the immune function deterioration is preferably one selected from the group consisting of a viral infectious disease such as a cold, an allergic disease such as an inflammatory disease, an atopy, chronic fatigue, and cancer, but is not limited thereto. And all diseases caused by immune function deterioration known to those skilled in the art are included in the present invention. The composition of the present invention may also be included as an adjuvant of a vaccine.

The present invention provides a method for preventing, ameliorating or treating infectious inflammatory diseases comprising administering to a subject in need thereof an effective amount of tryptophanyl-tRNA synthetase as an active ingredient.

The present invention provides a use for preparing an agent for preventing, ameliorating or treating infectious inflammatory diseases comprising tryptophanyl-tRNA synthetase as an active ingredient.

The present invention provides a method for immune enhancement comprising administering to a subject in need thereof an effective amount of tryptophanyl-tRNA synthetase as an active ingredient.

The present invention provides an application for preparing an agent for immune enhancement containing tryptophanyl-tRNA synthetase as an active ingredient.

The said "effective amount" of the compound of the present invention refers to an amount which, when administered to a subject, indicates an improvement, treatment and prophylactic effect of infectious inflammatory diseases, and the said "subject" may be an animal, preferably a mammal, particularly a human, animal including livestock, or may be an animal derived cell, tissue, organ, or the like. The subject may be a patient or a domestic animal requiring treatment.

Advantageous Effect

Accordingly, the present invention provides a pharmaceutical composition and a veterinary composition for treatment or prevention of infectious inflammatory diseases comprising tryptophanyl-tRNA synthetase as an active ingredient, a food composition for prevention and improvement, and a composition for immune enhancement, which comprises tryptophanyl-tRNA synthetase as an active ingredient. The composition of the present invention is particularly useful for preventing or treating diseases of humans and animals caused by bacterial, viral or fungal infections by inhibiting infections such as bacteria and viruses at an early stage by activating innate immune responses.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 8A shows that the secretion amounts of MIP-1α, TNF-α, MIP-1β, IL-6 and IL-8 were analyzed using image Lab 4.1 software after treating PBMC cells with full length-TrpRS and mini-TrpRS; FIG. 8B shows results of ELISA; and FIG. 8C shows RT-PCR for confirming the expression levels of TNF-α, MIP-1α and MIP-1β in cultured supernatant cultured in PBMC.

FIG. 10A-C shows the results of ELISA for the amount of MIP-1α in PBMC-derived macrophages, THP-1 cells, THP-1 derived macrophages and J774A.1 cells, and the amount of TNF-α, MIP-1α MCP-1 protein as determined by ELISA and RT-PCR, respectively.

DETAILED DESCRIPTION OF THE INVENTION

Hereinafter, the present invention will be described in detail.

However, the following examples are illustrative of the present invention, and the scope of the present invention is not limited to the following examples.

Example 1

The Tryptophanyl-tRNA Synthetase (TrpRS) Secreted from Bacterial Infected Peripheral Blood Mononuclear Cells Example 1-1. Identification of Aminoacyl-tRNA Synthetase Secreted from Bacterial and Fungal Infected Human Peripheral Blood Mononuclear Cells Immunoblot experiments were conducted to determine the type of aminoacyl-tRNA synthetase (ARS) secreted from human peripheral blood mononuclear cells (PBMC) infected with bacteria (FIG. 1). Bacteria and fungi, *Salmonella typhimurium* (*S. typhimurium*, ATCC 14028), *Listeria monocytogenes* (*L. monocytogenes*, ATCC 15313), *Escherichia coli* (*E. coli*, ATCC 10798), *Staphylococcus aureus* (*S. aureus*, ATCC 25923), *Candida albicans* (*C. albicans*, ATCC 10231), were obtained from the Korea Microbial Conservation Center and the Microbiological Resource Center, and were cultured periodically in nutrient broth or brain heart infusion (BD biosciences). The bacteria used for the infection experiment were cultured overnight, and were obtained at a density of $1 \times 10^8$ CFU. The CFU was estimated using an absorbance at 600 nm and a calibration curve prepared beforehand. In the bacterial infection experiment of this example and another example, the obtained bacteria were washed in PBS and resuspended in serum-free RPMI medium or PBS. Human PBMC were cultured at a density of $1 \times 10^6$ cells/well for one hour and infected with $1 \times 10^6$ CFU of *S. typhimurium* (MOI=1) or *L. monocytogenes* (MOI=1). The supernatants cultured for two hours after infection were precipitated by TCA and immunoblot experiments were performed on various kinds of ARS.

Figures 1A, 1B:
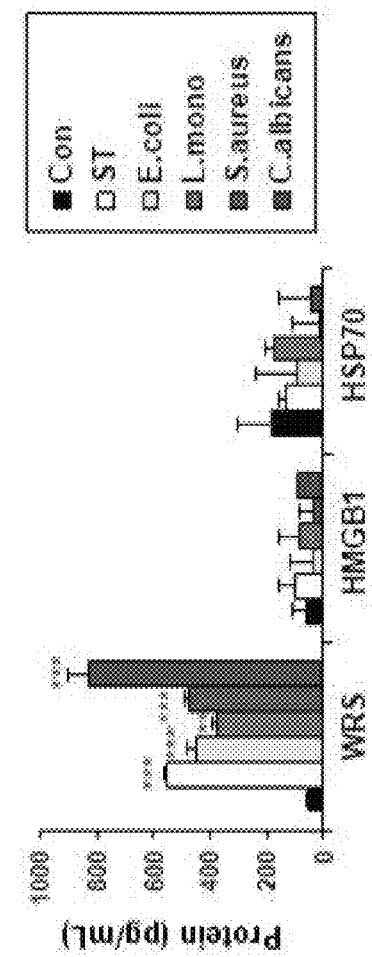
FIG. 1A shows the result of western blot analysis of TrpRS (WRS) of human peripheral blood mononuclear cell supernatant (SUP) and whole cell lysate (WCL) infected with *S. typhimurium*.
FIG. 1B shows the result of ELISA for the representative amount of TrpRS, HMGB-1 and HSP70 protein in culture supernatant of human peripheral blood mononuclear cells infected by bacteria and fungi.

As a result, the only full-length TrpRS, 53 kDa, was detected in the culture supernatant among the ARSs including secretory ARS (TrpRS, GRS, KRS, DRS), AIMP1 (a cofactor of ARS complexes) and ARS (TrpRS, MRS, HRS, GRS) containing the WHEP domain. This shows that the ARS secreted after bacterial infection is TrpRS (WRS) (FIG. 1A). It was also confirmed that full-length WRS was secreted from human peripheral blood mononuclear cells by infection with *S. typhimurium* and *L. monocytogenes* as well as by *E. coli*, *S. aureus* and *C. albicans* (FIG. 1B). This indicates that TrpRS (WRS) is more likely to be secreted in response to general bacterial and fungal infections than to certain bacteria.

Example 1-2. Kinetic Analysis of TrpRS and TNF-α Secretion

Figures 2A, 2B:
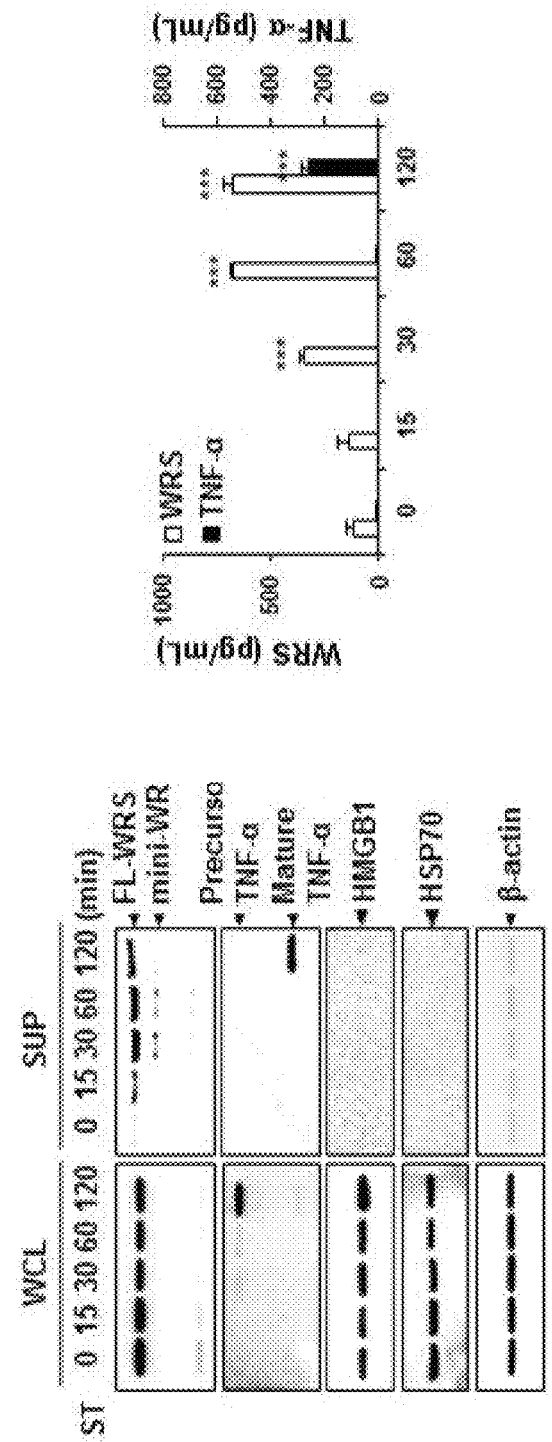
FIG. 2A shows the result of western blot analysis showing the secretion pattern of tryptophanyl-tRNA synthetase (TrpRS), tumor necrosis factor alpha (TNF-α), HMGB-1 and HSP70 secreted by *S. typhimurium*-infected human peripheral blood mononuclear cells over time.
FIG. 2B shows the results of ELISA showing the measurement of TNF-α and TrpRS produced in the culture supernatant of human peripheral blood mononuclear cells infected with *S. typhimurium* over time.

The secretion patterns of tryptophanyl-tRNA synthetase (TrpRS), tumor necrosis factor alpha (TNF-α), HMGB1, and heat shock protein (HSP70) was analyzed in human peripheral blood mononuclear cells (PBMC) infected with *S. typhimurium* from time to time right after infection (FIG. 2). Human PBMC were infected with *S. typhimurium* (MOI=1), and whole cell lysate (WCL) and culture supernatant were obtained at 0, 15, 30, 60, and 120 min, and immunoblot experiments were performed (FIG. 2A).

As a result, TrpRS in cultured supernatants was detected from 15 minutes after infection and increased for up to 120 minutes after infection. Also, the amount of TrpRS in WCL tended to decrease slightly with time after infection. Therefore, TrpRS is secreted to the outside of the cell from the beginning after infection. In addition, in the whole cell lysate, the TNF-α precursor (precursor TNF-α) was generated from 30 minutes after infection and was detected at 120 minutes, TNF-α (Mature TNF-α) was detected in trace amounts up to 120 minutes after infection. TNF-α (Mature TNF-α) was detected in the culture supernatant at 120 min. In other words, TrpRS is secreted to the outside of the cell within a short time after the infection, and it is found that it significantly precedes the secretion of TNF-α in time.

On the other hand, HMGB-1 and HSP70 were not detected in the culture supernatant over time after infection, whereas HMGB-1 and HSP 70 in all cell lysates were constantly detected with time after infection. Thus, HMGB-1 and HSP70 are not affected by bacterial infection.

In addition, the amounts of TrpRS and TNF-α secreted in the culture supernatant after bacterial infection were measured by ELISA at 0, 15, 30, 60, and 120 min after infection (FIG. 2B). As observed in the immunoblot experiment, TrpRS present in the culture supernatant increased significantly from 15 minutes after infection to 60 minutes after infection, but TNF-α present in the culture supernatant started to increase from 60 minutes after infection.

Example 1-3. Determination for Bacterial Infection and Pyroptosis

Figure 3:
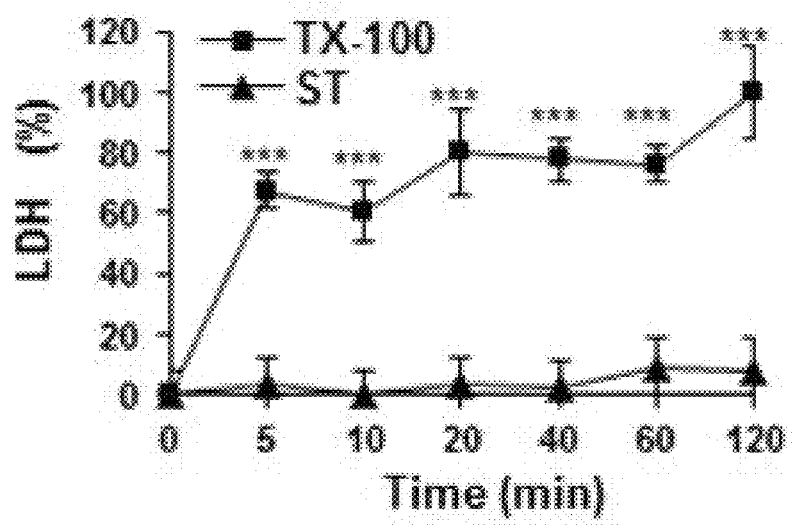
FIG. 3 shows a result of lactate dehydrogenase (LDH) assay to determine whether pyroptosis occurs in human peripheral blood mononuclear cells infected with *S. typhimurium*.

It was investigated whether TrpRS secretion in human peripheral blood mononuclear cells (PBMC) infected with *S. typhimurium* observed in Example 1-2 was caused by pyroptosis (FIG. 3). The pyroptosis was confirmed by assay of lactate dehydrogenase (LDH; a signature of cell death). In detail, human PBMCs were infected with *S. typhimurium*, and then LDH levels in culture supernatants at 0, 5, 10, 20, 40, 60, and 120 min after infection were measured using the LDH assay kit (Takara Bio, Inc.). 1% TX-100 treated PBMC was used as a positive control.

As a result, in the culture supernatant of the positive control (1% TX-100), the amount of LDH, a marker of pyroptosis, increased rapidly with time, whereas the culture supernatant of *S. typhimurium*-infected PBMC reached 120 minutes after infection with no significant change in the amount of LDH, indicating that LDH was not expressed during this period. Therefore, these results verify that PBMC after bacterial infection excretes TrpRS outside the cell by active secretion rather than pyroptosis (FIG. 3).

Figure 4:
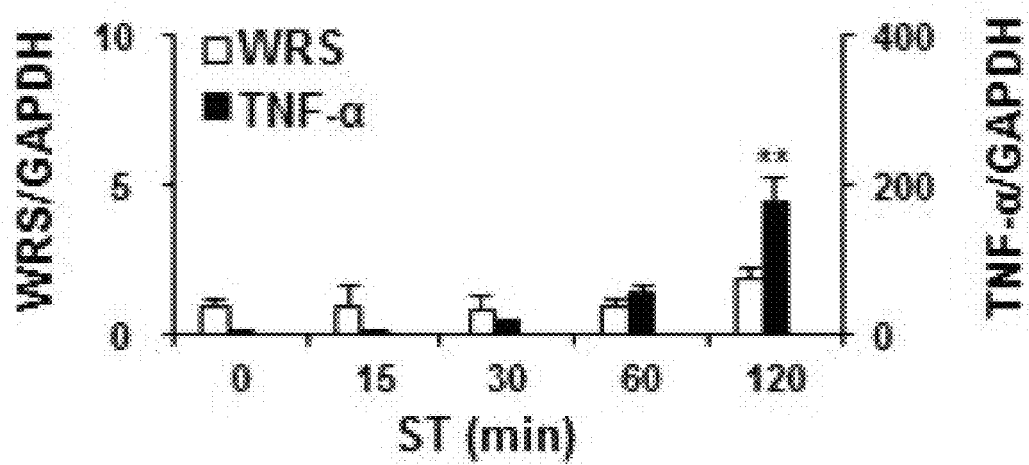
FIG. 4 shows real time-PCR results showing the mRNA levels of TNF-α and TrpRS produced in human peripheral blood mononuclear cells infected with *S. typhimurium* over time.

Example 1-4. Evaluation on Bacterial Infection and Expression Levels of TNF-α and TrpRS The expression patterns of TNF-α and TrpRS (WRS) genes in human peripheral blood mononuclear cells (PBMC) infected with *S. typhimurium* were examined by RT-PCR and ELISA (FIG. 4). Human PBMC were infected with *S. typhimurium*, and cells were obtained at 0, 15, 30, 60, 120 minutes after the infection, and the mRNA levels of TNF-α and TrpRS were measured. RNA was extracted according to the experimental method of RNeasy kit (Qiagen, Hilden, Germany) and reverse transcribed with M-MLV reverse transcriptase (Invitrogen, Carlsbad, Calif., USA), then quantitative real-time PCR (quantitative RT-PCR) was performed with the following primers. The level of GAPDH mRNA was determined as an internal control.

```
hTNF-α Forward:
                                         (SEQ ID NO: 9)
5-GGAGAAGGGTGACCGACTCA-3 hTNF-α Reverse:
                                         (SEQ ID NO: 10)
5-CTGCCCAGACTCGGCAA-3 hTrpRS Forward:
                                         (SEQ ID NO: 11)
5-AAGAATTCATGCCCAACAGTGAGCCC-3 hTrpRS Reverse:
                                         (SEQ ID NO: 12)
5-AACTCGAGCTACCCTGGAGGACAGTCAGCCTT-3

GAPDH forward:
                                         (SEQ ID NO: 13)
5-CGCTCTCTGCTCCTCCTGTTC-3

GAPDH reverse:
                                         (SEQ ID NO: 14)
5-TTGACTCCGACCTTCACCTTCC-3
```

As a result, it was confirmed that the level of TNF-α mRNA increased from 30 minutes to 120 minutes, while the level of TrpRS mRNA did not significantly change until 120 minutes after infection (FIG. 4). This suggests that TrpRS secreted after infection is one, which is already present in the cell without its gene expression induced after infection. It was also confirmed that mRNA of TNF-α, a major proinflammatory cytokine induced by bacterial infection, increased greatly from 30 minutes to 12 minutes after infection. The TNF-α mRNA was significantly increased up to 60 minutes after 40 minutes of infection and the increase in the amount of TNF-α secretion observed in Example 1-2 was detected from 60 minutes after the infection, indicating that the secretion of TrpRS is already occurring before TNF-α production.

Figure 5:
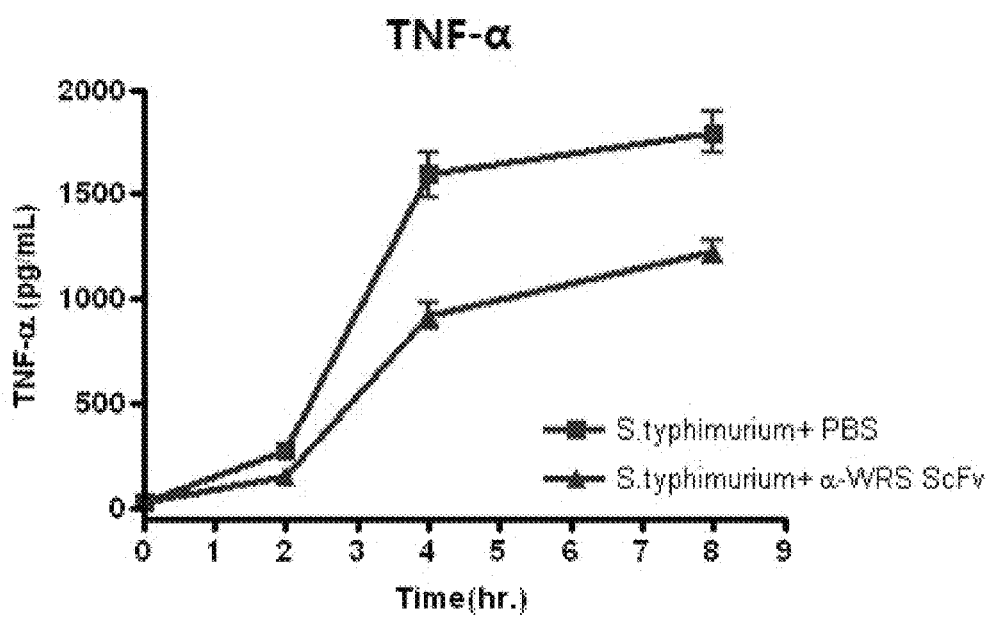
FIG. 5 shows the results of TrpRS antibody treatment and ELISA test to examine the effect of TrpRS on the secretion of TNF-α in human peripheral blood mononuclear cells infected with *S. typhimurium*.

Example 1-5. Relationship Between TrpRS and TNF-α Secreted after Bacterial Infection In Example 1-2, it was confirmed that TrpRS and TNF-α were secreted with time difference in *S. typhimurium*-infected human peripheral blood mononuclear cells (PBMC). In addition, it was observed that TNF-α was not secreted in the absence of TrpRS secretion at the early stage of infection in the PBMC infected with Heat-killed *S. typhimurium*. Thus, the functional relationship between TrpRS secreted after infection and TNF-α was examined (FIG. 5). PBMCs were treated with TrpRS function-neutralizing antibody (antibody concentration 10 µg/mL) and infected with *S. typhimurium* (MOI=1). Then the secretion pattern of TNF-α was measured at 0, 2, 4, and 8 h, by ELISA.

As a result, in PBMC (*S. typhimurium*+α-WRS ScFv), which had reduced the function of TrpRS by antibody treatment, it was observed that the amount of TNF-α was significantly decreased compared with PBS-treated control PBMC (*S. typhimurium*+PBS). This suggests that TrpRS plays an important role in the production and secretion of TNF-α. These results suggest that TrpRS may be the first factor to control TNF-α production, especially in bacterial infections.

Example 1-6 Aminoacyl t-RNA Synthetase Secreted from Virus-Infected Human Peripheral Blood Mononuclear Cells ELISA experiments were performed to determine the amount of aminoacyl t-RNA synthetase (ARS) secreted by human peripheral blood mononuclear cells (PBMC) over time after viral infection (FIG. 6). The virus was titrated by respiratory syncytial virus A2 (RSV A2) and PR8 influenza virus (Influenza A/Puerto Rico/8/1934 virus) by standard plaque analysis. Human PBMCs were each infected with the human PBMC for 2 hours and incubated for 24 hours. Culture supernatants were harvested at each hour post-infection and levels of TrpRS (WRS) were measured by ELISA.

Figure 6B:
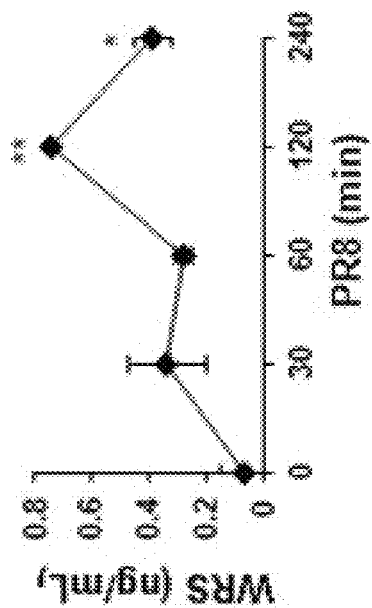
FIG. 6A shows the amount of TrpRS (WRS) protein in the culture supernatant of human peripheral blood mononuclear cells infected with respiratory syncytial virus (RSV) and FIG. 6B shows human peripheral blood mononuclear cells infected with PR8 influenza virus, respectively. The results obtained by ELISA are shown.
Figure 6A:
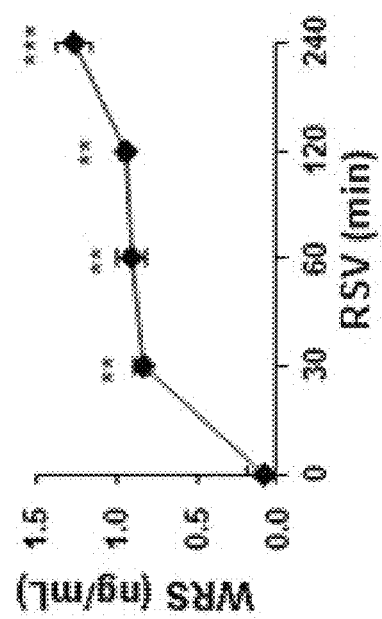

As a result, the concentration of TrpRS increased with time in RSV-infected cells (FIG. 6A), while in the PR8-infected cells, the TrpRS concentration increased up to 120 minutes after infection but decreased after 120 minutes (FIG. 6B). This shows that TrpRS is secreted in response to viral infection.

Example 2

Figure 7:
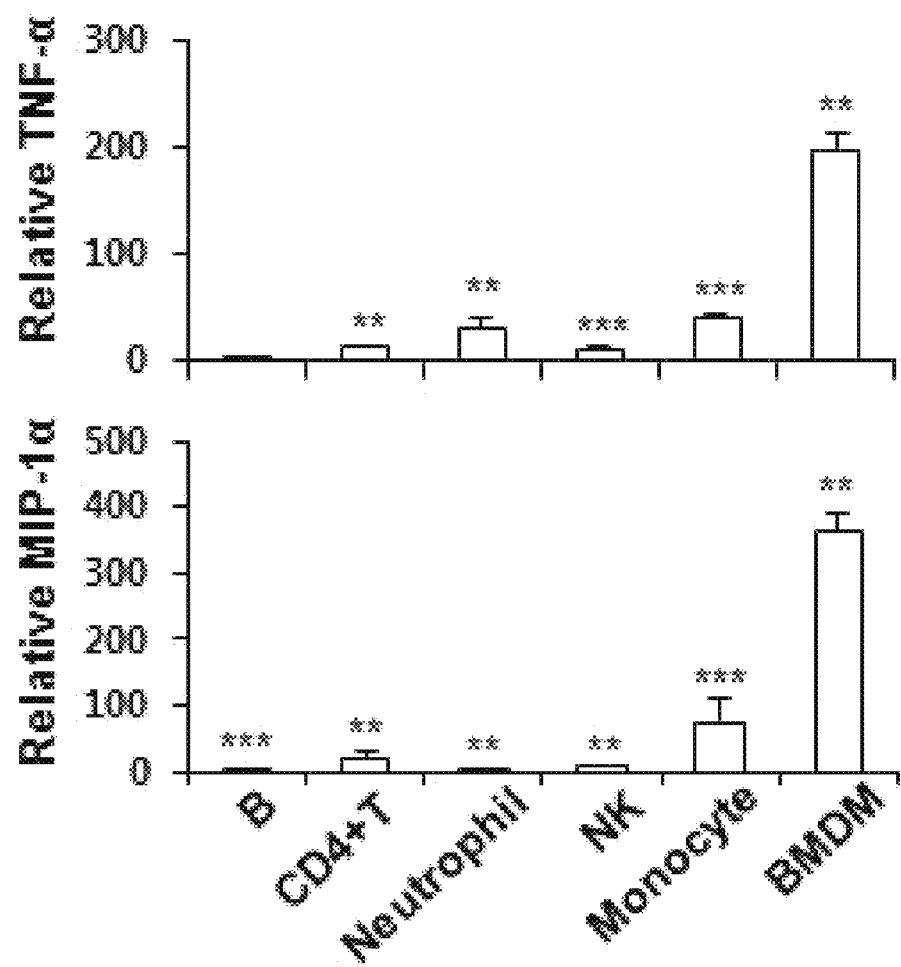
FIG. 7 shows ELISA results showing the secretion pattern of TNF-α and MIP-1α in TrpRS-treated immune cells.

Increased Secretion of Monocyte/Macrophage-Specific TNF-α and MIP1-α by TrpRS To investigate the types of immune cells responsive to secreted TrpRS, various immune cells were treated with TrpRS and cells that secrete cytokines such as TNF-α and MIP1-α were examined (FIG. 7). Primary B cells, T cells, neutrophils, natural killer cells (NK), and peripheral blood mononuclear cells (NK) and monocyte of mice were isolated using a mouse microbead isolation kit (Miltenyi, Bergisch Gladbach, Germany) The obtained cells showed more than 95% purity when analyzed by flow cytometry. Bone marrow-derived macrophages (BMDM) were prepared by differentiating for 6 to 7 days in the presence of M-CSF (20 ng/mL). Bone marrow-derived dendritic cells (BMDC) were prepared by differentiating for 6 to 7 days in the presence of GM-CSF (20 ng/ml) and IL-4 (20 ng/ml) Immunocytes were cultured for 18 hours in the presence of the control, full-length TrpRS (TrpRS-full, 100 nM), mini-TrpRS (TrpRS-mini, 100 nM), and LPS (100 ng/ml), respectively, and the amount of TNF-α and MIP1-α protein present in the culture supernatant was measured by ELISA kit (BD Sciences, San Jose, Calif., USA and R & D systems). TrpRS all used a protein having the amino acid sequence of human TrpRS (human TrpRS) in the experiment.

As a result, LPS significantly induced TNF-α secretion in most of the immune cells, whereas full-length TrpRS showed the greatest effect in monocytes and BMDM (Table 1, top of FIG. 7). Full-length TrpRS treated with heat or trypsin had no effect on TNF-α secretion (data not shown). In addition, mini-TrpRS had no effect on TNF-α secretion. For MIP1-α, the increase effect of TrpRS was confirmed only in monocytes and BMDM of mice treated with full-length TrpRS (Table 2, FIG. 7 bottom). These results indicate that TrpRS specifically activates monocytes and macrophages, and monocytes and macrophages secrete TNF-α and MIP1-α as a result of activation.

TABLE 1

Effect of TrpRS on the secretion of TNF-α in immune cells

| TNF-α (pg/mL) | Control | Full-length TrpRS | Mini TrpRS | LPS |
|---|---|---|---|---|
| B cell | 107 ± 91 | 132 ± 34 | 79 ± 44 | 227 ± 38 |
| CD4 + T cell | 2 ± 4 | 99 ± 20 | 134 ± 125 | 516 ± 4 |
| Monocyte | 69 ± 7 | 511 ± 43 | 10 ± 13 | 975 ± 24 |
| BMDM | 17 ± 11 | 3299 ± 175 | 44 ± 35 | 3573 ± 7 |
| BMDC | 61 ± 11 | 1083 ± 105 | 148 ± 119 | 3557 ± 66 |
| Neutrophil | 21 ± 4 | 597 ± 38 | 65 ± 4 | 3765 ± 130 |
| NK | 28 ± 8 | 259 ± 14 | 3 ± 8 | 2373 ± 200 |

TABLE 2

Effect of TrpRS on the secretion of MIP1-α in immune cells

| MIP1-α (pg/mL) | Control | Full-length TrpRS | Mini TrpRS | LPS |
|---|---|---|---|---|
| B cell | 57 ± 2 | 124 ± 2 | 85 ± 23 | 391 ± 49 |
| CD4 + T cell | 8 ± 1 | 141 ± 13 | 9 ± 1 | 552 ± 7 |
| Monocyte | 7 ± 0 | 533 ± 27 | 6 ± 1 | 1246 ± 7 |
| BMDM | 7 ± 7 | 2647 ± 205 | 8 ± 1 | 3369 ± 45 |
| BMDC | 32 ± 5 | 34 ± 34 | 50 ± 16 | 980 ± 78 |
| Neutrophil | 6 ± 3 | 26 ± 3 | 7 ± 5 | 3529 ± 8 |
| NK | 6 ± 3 | 36 ± 1 | 3 ± 1 | 1157 ± 41 |

Example 3

Activation of Innate Immune Response by TrpRS

Example 3-1. Chemokines Secreted by TrpRS-Stimulated Bone Marrow-Derived Macrophages The types and amounts of chemokines secreted by BMDM in response to TrpRS were examined (Table 3). BMDM was treated with full-length TrpRS (30, 100 nM) or mini-TrpRS (100 nM) for 18 hours, and the presence of chemokines in the culture supernatant was measured by ELISA.

In addition, human PBMC cells were treated with human full length-TrpRS (FL-WRS) and mini-TrpRS (mini-WRS) for 18 hours and cytokines present in the culture supernatant were measured using ELISA. RT-PCR experiments were used to measure the expression levels of cytokines and chemokines.

```
hTNF-α Forward:
                                    (SEQ ID NO: 9)
5-GGAGAAGGGTGACCGACTCA-3 hTNF-α Reverse:
                                    (SEQ ID NO: 10)
5-CTGCCCAGACTCGGCAA-3
```

-continued hTrpRS Forward:
(SEQ ID NO: 11)
5-AAGAATTCATGCCCAACAGTGAGCCC-3 hTrpRS Reverse:
(SEQ ID NO: 12)
5-AACTCGAGCTACCCTGGAGGACAGTCAGCCTT-3 hMIP-1α Forward:
(SEQ ID NO: 15)
5-ACCATGGCTCTCTGCAACCA-3 hMIP-1α Reverse:
(SEQ ID NO: 16)
5-TTAAGAAGAGTCCCACAGTG-3 hMIP-1β Forward:
(SEQ ID NO: 17)
5-AGCCTCACCTCTGAGAAAACC-3 hMIP-1β Reverse:
(SEQ ID NO: 18)
5-GCAACAGCAGAGAAACAGTGAC-3

GAPDH forward:
(SEQ ID NO: 13)
5-CGCTCTCTGCTCCTCCTGTTC-3

GAPDH reverse:
(SEQ ID NO: 14)
5-TTGACTCCGACCTTCACCTTCC-3

As a result, full-length TrpRS induced chemokines such as MIP-1α, MCP-1, and IP-10 and cytokines such as TNF-α and IL-1β in a concentration-dependent manner. On the contrary, mini-TrpRS had no effect on cytokine secretion and chemokine secretion (Table 3). In addition, full-length TrpRS induced the secretion of chemokines and cytokines such as TNFα, MIP-1α, MIP-1β, IL-6 and IL-8, but mini-TrpRS had no effect on cytokine and chemocyte secretion (FIG. 8A). In addition, it was confirmed that the expression levels of TNFα, MIP-1α, MIP-1β, IL-6 and IL-8 were increased in PBMC cells treated with full length-TrpRS (FIGS. 8B & 8C)

Thus, it was confirmed that Full length-TrpRS induces the expression and secretion of cytokines, in contrast to mini-TrpRS.

TABLE 3

The cytokines and chemokines secreted by TrpRS-stimulated bone marrow-derived macrophages (BMDM)

| Cytokines | Control | Full-length TrpRS | | Mini TrpRS |
|---|---|---|---|---|
| | | 30 nM | 100 nM | 100 nM |
| TNF-α | 17 ± 11 | 2159 ± 691 | 3299 ± 175 | 44 ± 35 |
| MIP-1α | 7 ± 7 | 1621 ± 49 | 2647 ± 205 | 8 ± 1 |
| MCP-1 | 1 ± 1 | 793 ± 39 | 1430 ± 114 | 14 ± 19 |
| IP-10 | 43 ± 12 | 283 ± 15 | 493 ± 76 | 0 ± 10 |
| IL-1β | 14 ± 4 | 59 ± 4 | 135 ± 14 | 16 ± 11 |

Example 3-2. Effect of TrpRS on Immune Cell Fluidity

Figure 9:
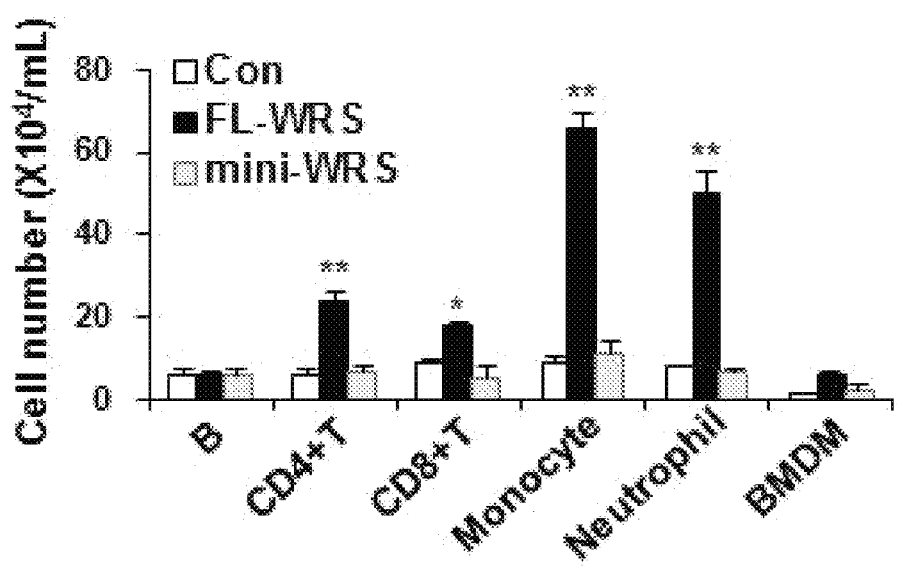
FIG. 9 shows the results of a transwell migration assay showing the effect of the culture supernatant of TrpRS-treated bone marrow-derived macrophages (BMDM) on the immune cell fluidity.

The effect of TrpRS on the fluidity of immune cells was examined using a transwell migration assay (FIG. 9). Bone marrow-derived macrophages (BMDM) were treated with full-length TrpRS (FL-WRS, 100 nM) or mini-TrpRS (mini-WRS, 100 nM) and cultured for 18 hours, then transferred to a 24-well plate. Primary immune cells and BMDM were placed in the upper part of the migration chamber and incubated at 37° C. for 4 hours.

As a result, it was observed that the culture supernatant of full-length TrpRS-treated BMDM (TrpRS-F) greatly increased infiltration of monocytes and neutrophils. In contrast, the TrpRS protein itself (data not shown) or the mini-TrpRS-treated culture supernatant (TrpRS-M) had no effect on cell migration.

Example 3-3. Effect of TrpRS on the Secretion of MIP-1 and TNF-α in Various Immune Cells Effects of TrpRS on secretion of MIP-1 and TNF-α in various immune cells including PBMC-derived macrophages, THP-1 cells, THP-1 derived macrophages and J774A.1 cells were investigated by ELISA experiments and RT-PCR respectively. Each immune cell was treated with full length-TrpRS (FL-WRS, 100 nM) or mini-TrpRS (mini-WRS, 100 nM) and cultured for 18 hours. The culture was transferred to a 96-well plate and subjected to ELISA. The BMDM cells were treated with full-length TrpRS or mini-TrpRS and mRNA was extracted and RT-PCR was performed.

As a result, it was confirmed that full length-TrpRS in PBMC-derived macrophages, THP-1, THP-1 derived macrophages and J774A.1 induce the secretion of MIP-1α (FIG. 10A). In BMDM cells, it was confirmed that full length-TrpRS, which is not mini-TrpRS induces the production of TNF-α, MIP-1α and MCP-1 proteins (FIG. 10B) and induces mRNA expression (FIG. 10C).

Example 3-4. TrpRS-Induced Neutrophil Accumulation in the Body

To investigate the effect of TrpRS on the innate immune response in the body, intraperitoneal neutrophil recruitment following TrpRS injection was observed (FIG. 11). PBS, full-length TrpRS (3, 10, 30 μg), or mini-TrpRS (30 μg) were injected into the peritoneal cavity of mice (6 to 10 per group) and the peritoneal cavity was drained after 4 hours. The peritoneal effusion was extracted and the ratio of Ly6C+ Ly6G+cell group was measured by flow cytometry (FIGS. 11A & 11B), and MIP1-α present in the peritoneal effusion was measured by ELISA (FIG. 11C). The statistical significance of the comparison between the PBS-treated negative control and the results of each experimental condition was verified by one-way Anova test using GraphPad (ver. 4.0) software. * $p<0.001$,  $p<0.01$ As a result of flow cytometry, concentration-dependent tendency was dramatically observed only in the full-length TrpRS injected mice (TrpRS-F3, TrpRS-F10 and TrpRS-F30), whereas mini-TrpRS (TrpRS-M30) did not achieve this effect (FIG. 11B). That is, this result shows that full-length TrpRS can induce innate immune responses that cause neutrophil concentration in vivo. Similarly, MIP1-α, which was measured in the peritoneal effusion, increased in a concentration-dependent manner only in the full-length TrpRS injected mice (TrpRS-F3, TrpRS-F10, and TrpRS-F30), and did not increase in mini-TrpRS injected mice (TrpRS-M30).

Figure 11A:
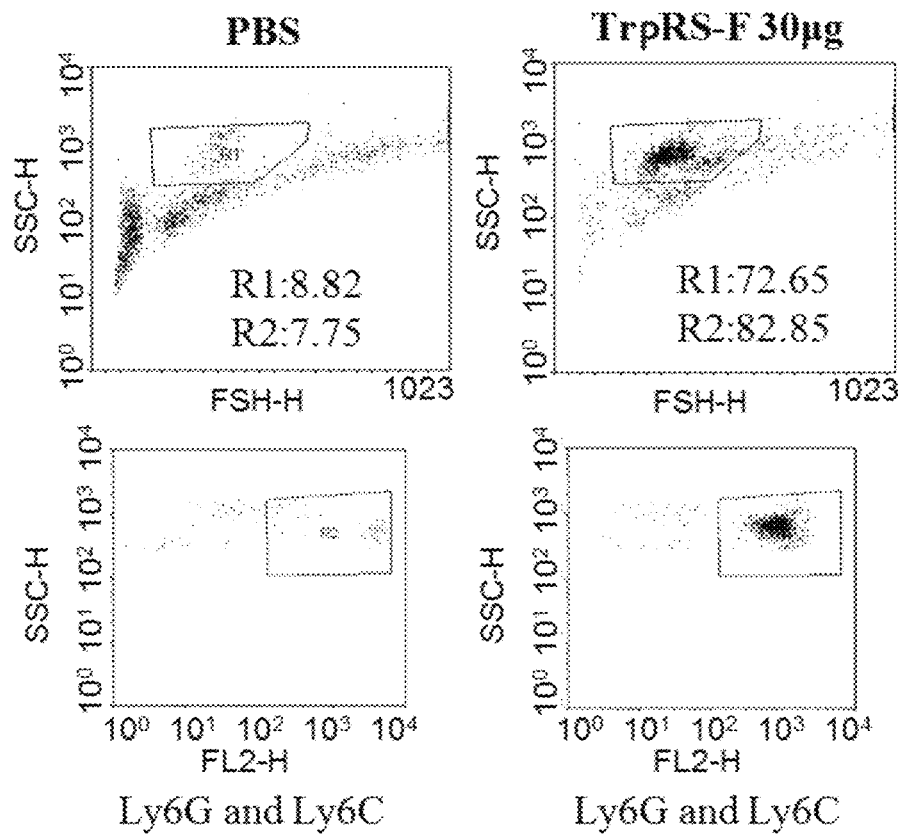
FIG. 11A-D shows the result of flow cytometry analysis showing the neutrophil recruitment in the mouse peritoneal cavity injected with TrpRS, the result of ELISA showing the secretion amount of MIP1-α, and the results of flow cytometric analysis showing the number of neutrophil, macrophage, and bone marrow cells.
Figure 11B:
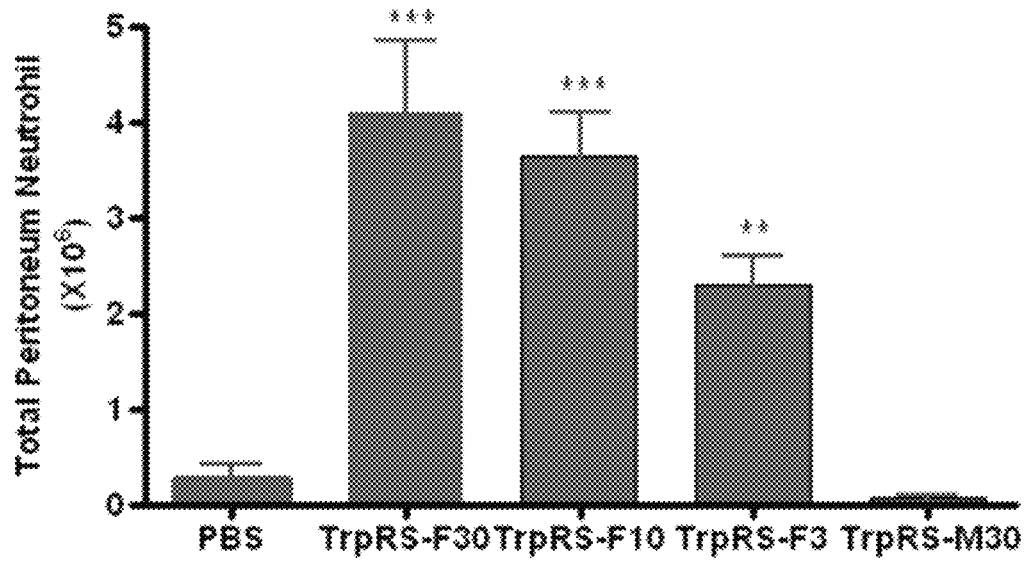
Figure 11C:
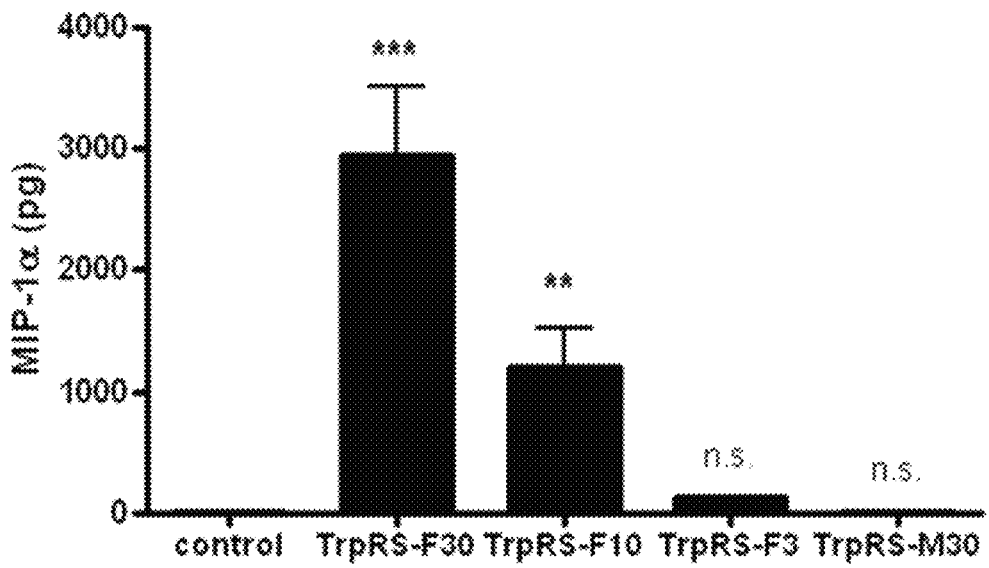
Figure 11D:
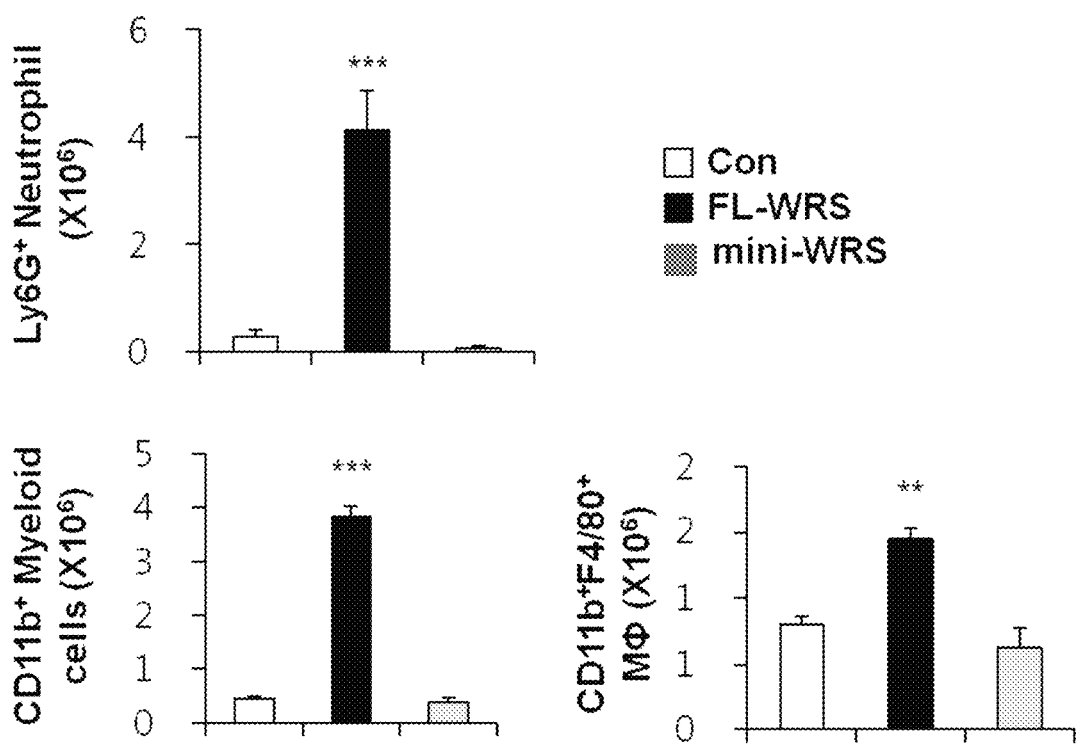

In addition, the number of Ly6G$^+$ neutrophils, CD11b$^+$ myeloid cells, and CD11b$^+$F4/80$^+$ macrophages increased in the full length-TrpRS (FL-WRS) treated peritoneum as compared to the mini-TrpRS and PBS-infected controls (FIG. 11D).

Figure 12A:
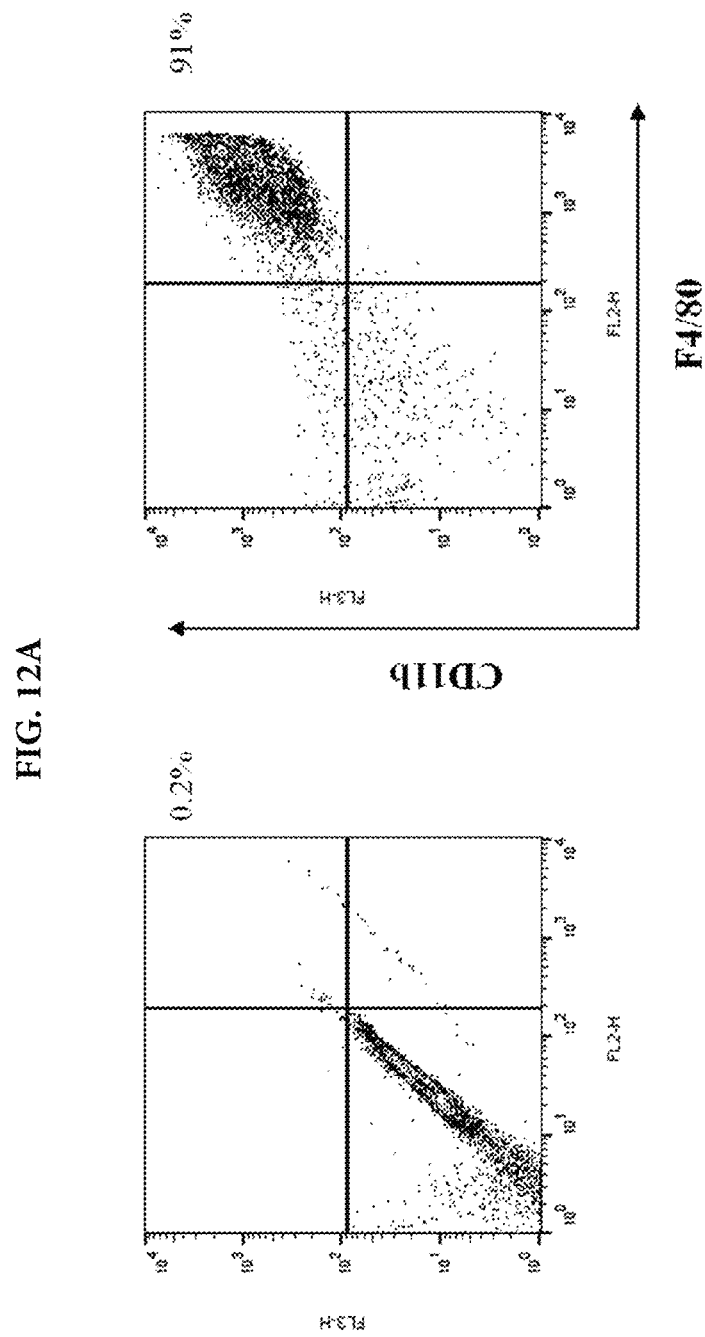
FIG. 12A-B shows flow cytometric analysis results showing CD40, CD80, and CD86 protein expression patterns of TrpRS-treated bone marrow-derived macrophages.

Example 3-5. Effect of TrpRS on the Activation of Bone Marrow-Derived Macrophages The effect of TrpRS on bone marrow-derived macrophage (BMDM) activation was analyzed through the expression of activated macrophage markers and flow cytometry analysis (FIG. 12). Flow cytometric analysis using Cd11b and F4/80 of FIG. 11A indicates that bone marrow cells were well differentiated into BMDM for macrophage activation label analysis. Differentiated BMDM were treated with full-length TrpRS (30, 100 nM) or mini-TprRS (100 nM) and cultured for 18 h and CD40, CD80 and CD86 protein expression levels were measured by flow cytometry.

Figure 12B:
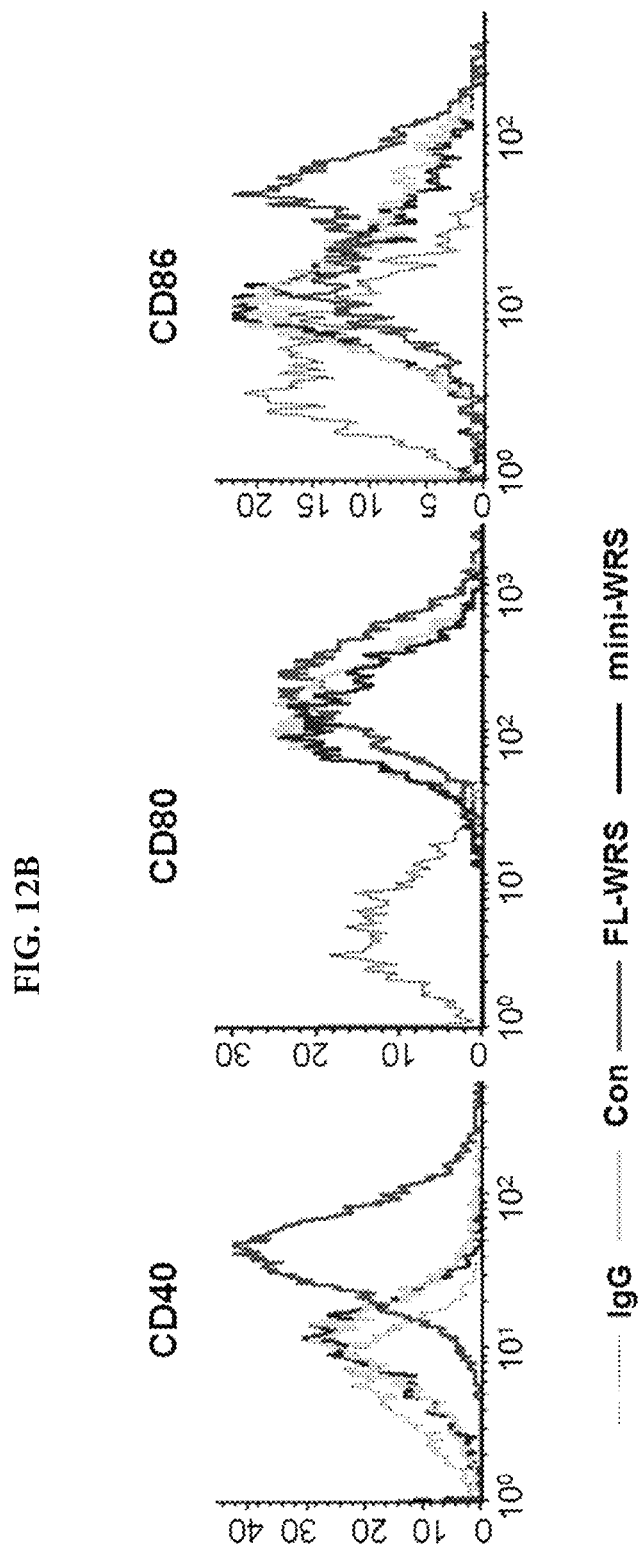

As a result, it was confirmed that the cell surface expression of CD40, CD80 and CD86, which are macrophage activation indicators, was abruptly increased only in the full-length TrpRS-treated BMDM (TrpRS-F) (FIG. 12B). The Mini-TrpRS-treated BMDM (TrpRS-M) was not significantly different from the control group. That is, this result verifies that full-length TrpRS promotes activation of macrophages.

Example 3-6. Effect of TrpRS on Phagocytosis of Bone Marrow-Derived Macrophages (BMDM)

Figure 13:
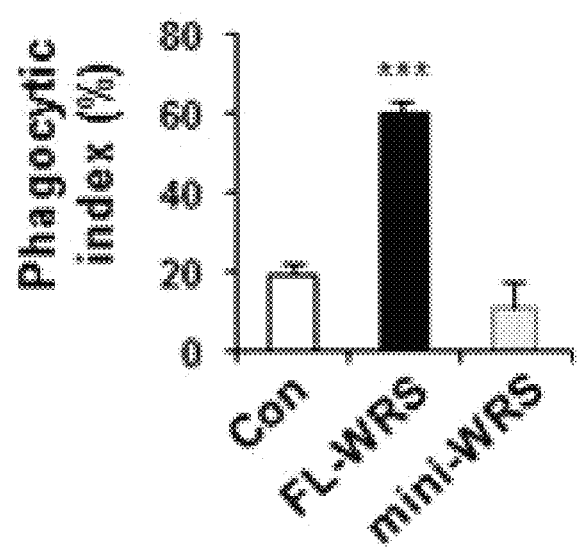
FIG. 13 shows the results of macrophage experiments using fluorescently-labeled *Escherichia coli* derived from the phagocytosis index of TrpRS-treated bone marrow-derived macrophages.

The effect of TrpRS on the phagocytosis of bone marrow-derived macrophages (BMDM) was investigated (FIG. 13). BMDM was cultured in 96-well culture dishes overnight, then replaced with RPMI medium without M-CSF, and cultured for 18 hours with full-length TrpRS (30 nM) or mini-TrpRS (30 nM). After washing the cells, 100 μL of fluorescently labeled E. coli bioparticles (Vybrant phagocytosis assay kit, Invitrogen) was added and cultured for 2 hours. After the culture medium was removed, the cells were treated with trypan blue (100 μL) for 1 minute to inhibit autofluorescence. Fluorescence signals due to macrophage were measured at 485 nm (excitation) and 520 nm (emission) to display the degree of phagocytic action (BMG Labtech, FLUOstar OPTIMA, Ortenberg, Germany). Statistical significance was verified by t-test using GraphPad (ver. 4.0) software. *** $p<0.0001$ As a result, the phagocytic index of full-length TrpRS-treated BMDM (TrpRS Full) was found to be 3 times higher than that of the control group. The Mini-TrpRS (TrpRS Mini) had no effect. Experimental results of Examples 3-1 to 3-4 show that full-length TrpRS induces innate inflammatory responses through macrophage activation.

Example 3-7. Effects of TrpRS on Macrophages

To investigate the effect of the full length-TrpRS-derived congenital immune response on macrophages, the following experiment was carried out using macrophage-depleted mice.

The splenocytes were removed from the spleen of normal mice and macrophage-nulled mice and the removal of macrophages was confirmed by flow cytometry. Separated splenocytes were prepared, cultured overnight in a 24-well culture dish, and treated with full length-TrpRS, and the secretion of TNF-α and MIP-1α was measured by ELISA.

Figure 14A:
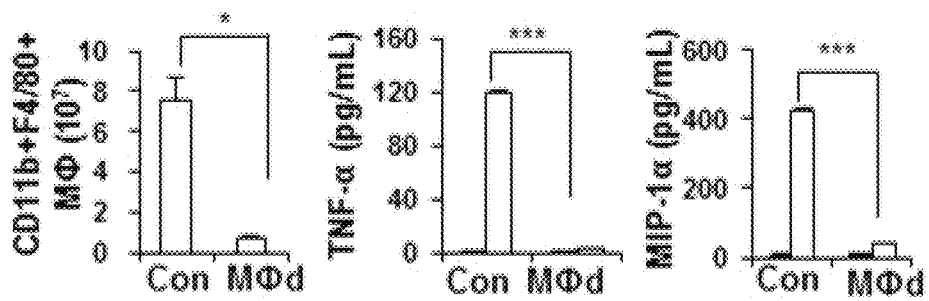
FIG. 14A-B shows the results of measurement of the amount of TNF-α and MIP-1α in the full length-TrpRS and mini-TrpRS-treated macrophages by ELISA, and the results of measurement of the number of CD11b$^+$ F4/80$^+$ cells in PEC (peritoneal exudate cells) and Ly6G$^+$ neutrophils by flow cytometry.
Figure 14B:
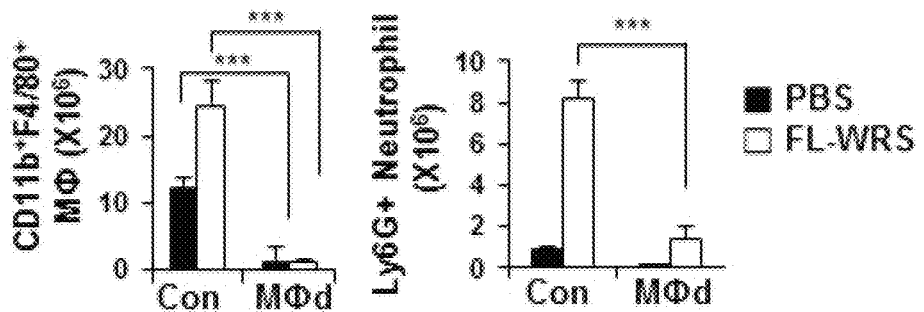

As a result, it was confirmed that the secretion amount of TNF-α and MIP-1α decreased with the decrease of macrophages (FIG. 14A). The decrease in macrophages in the body indicates that macrophages play a functional role in the immunostimulatory activity of full length-TrpRS, as the number of infiltrated neutrophils in the peritoneum decreases (FIG. 14B). This confirms that full length-TrpRS targets macrophages to activate the innate immune response.

Example 3-8. Effect of TrpRS on Macrophage Activity

The effect of TrpRS on bone marrow-derived macrophage activity was investigated. Alexa 647 labeled full-length TrpRS (FL-WRS) or mini-TrpRS (mini-WRS) were inoculated into the ear of mice and photographed 1 and 4 hours post-infection using in vivo imaging techniques. In addition, S. typhimurium labeled with Alexa 647 combined with Full length-TrpRS or mini-TrpRS was inoculated into the ear of GFP-LysM Tg mice capable of observing neutrophils and macrophages by GFP expression. To observe macrophages in mice, macrophages were photographed using in vivo imaging technology and counted Immuno-cellular dynamics were visualized using a custom-built video-rate laser-scanning confocal microscope imaging system (Choe et al., 2013; Seo et al., 2015). Three consecutive lasers were used as the fluorescent stimulus source. Three fluorescence colors emitted from the mice were detected as highly sensitive optoelectronic layer tubes at 488 nm (MLD, Cobolt), 561 nm (Jive, Cobolt) and 640 nm (MLD, Cobolt). And it was digitized by the 8-bit 3-channel frame grabber.

Figure 15A:
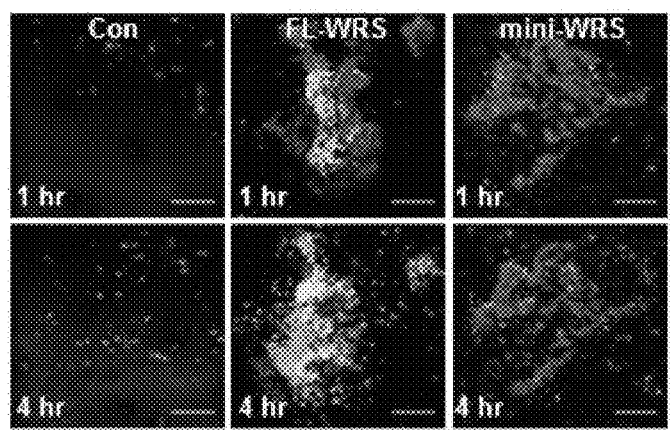
FIG. 15A-B shows the images (X20) obtained by injecting the full length-TrpRS and mini-TrpRS (red) labeled with Alexa 647 in the LysM-GFP transgenic mice, and the index of macrophage in the mice infected with *S. typhimurium*, which were injected with full length-TrpRS and mini-TrpRS.
Figure 15B:
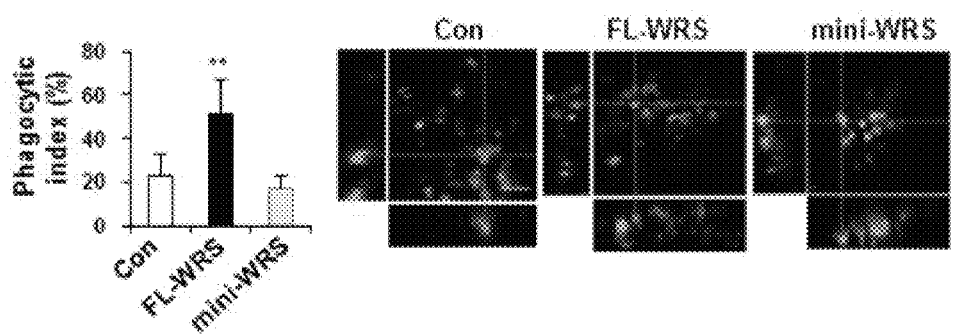

As a result, it was confirmed that infiltration of neutrophils and macrophages appeared at the site of full-length TrpRS inoculation instead of mini-TrpRS. Such an infiltration started at 1 hour after inoculation, and the amount of infiltration at 4 hours after inoculation was the highest (FIG. 15A). In addition, it was confirmed that phagocytic index of macrophage was increased in mice treated with full length-TrpRS (FL-WRS) as compared to mice treated with mini-TrpRS (mini-WRS) or PBS(Con) (FIG. 15B).

Example 4

TrpRS Inhibition-Devised Effect

Example 4-1. Preparation of Antibodies Specifically Binding to TrpRS

Figure 16:
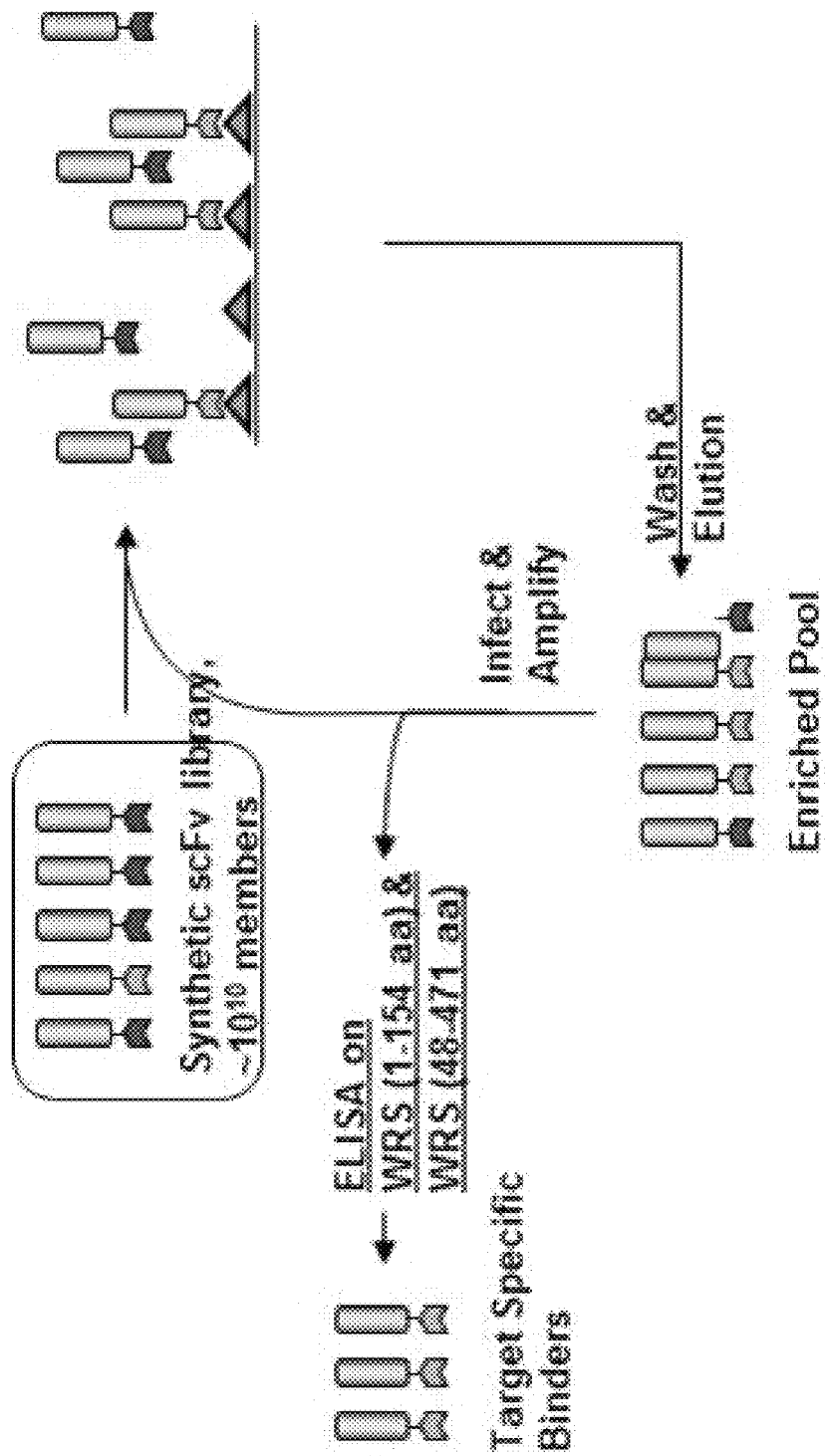
FIG. 16 schematically shows a process for producing an antibody specifically binding to TrpRS.

TrpRS was titrated with TrpRS-specific antibodies to further validate the protective role of TrpRS against infection. First, an antibody that specifically binds N154 peptide of human TrpRS was prepared by panning a library of phage display human single chain variable fragments (scFV) (FIG. 16) Immuno tubes were coated with TrpRS 10 and blocked with MPBS (PBS with 3% nonfat dried milk). Phage-displayed scFv library ($1\times10^{13}$ CFU) was added to 1 ml of mPBST, added to the immune tube, incubated for 2 hours and then washed 3-5 times with PBST. The bound phage was eluted with 1 mL of 100 mM trimethylamine and neutralized with 0.5 mL of 1 M Tris-HCl (pH 7.0). E. coli ER257 was infected with the eluted phage and cultured in LB medium containing 2% glucose and ampicillin for one day, and bacteria were collected from the medium logarithm. The bacteria were then cultured in 20 mL SB (3% Tryptone, 2% yeast extract, 1% MOPS, pH 7.0) supplemented with ampicillin to an OD600 of 0.5. VCSM13 helper phage ($1\times10^{11}$ PFU) was added and incubated at 37° C. for 1 hour, followed by kanamycin (70 μg/ml) and incubated overnight at 30° C. The supernatant was removed by centrifugation, and phage precipitation solution (4% PEG 8000 and 3% NaCl, final concentration) was added and mixed. After 30 minutes of incubation on ice, the precipitated phage were collected by centrifugation. After panning the library four times, individual scFv clones capable of binding TrpRS were screened. This process is illustrated in FIG. 16.

In order to confirm whether the prepared antibodies specifically bound to TrpRS affects the effect of TrpRS on infection, the following experiment was conducted. PBMC was treated with the prepared antibody (10 μg/mL) and infected with S. typhimurium (MOI=1) as described in Example 1 above. The secretion pattern of TNF-α in cell culture was measured by ELISA. In order to confirm whether scFv 4G1 binds to full length-TrpRS (FL-WRS) by selecting 4G1 clones, PBMC cell lysates were extracted and immunoblotted.

Figure 17A:
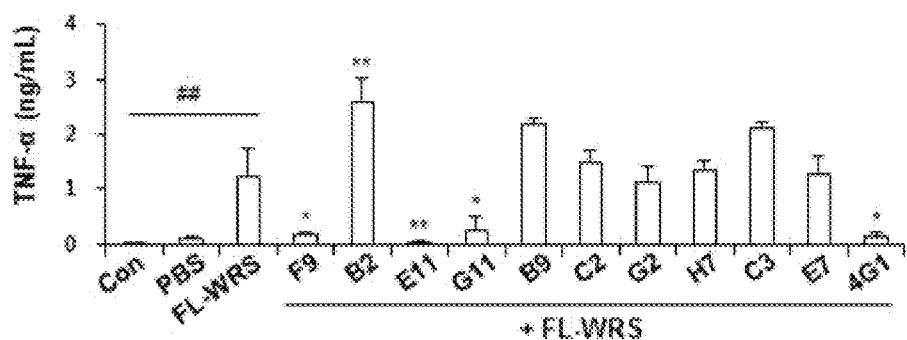
FIG. 17A-C shows the amount of TNF-α in THP-1 cells treated with full length-TrpRs and antibodies specific to TrpRS, the results of ELISA showing the effect of antibody (scFv 4G1) on TNF-α production in human PBMC cells, and the expression of recombinant protein binding to full length-TrpRS or mini-TrpRS using antibodies.
Figure 17B:
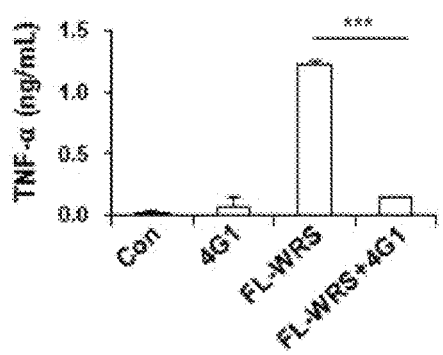
Figure 17C:
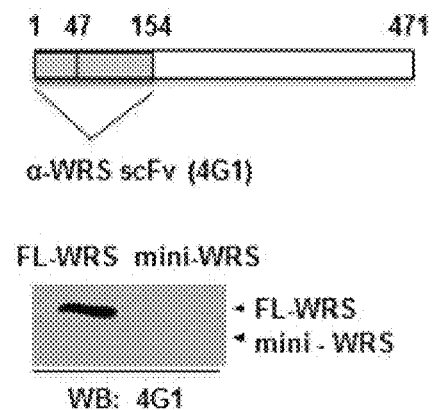

As a result, it was confirmed that the F9, E11, and 4G1 clones among some clones showed a decrease in the secretion amount of TNF-α of full length-TrpRS in human PBMC cells (FIG. 17A), while both only 4G1 treatment and full length-TrpRS and 4G1 treatment (FIG. 17B) decreased the amount of the secreted TNF-α. In addition, it was confirmed through immunoblotting that scFV 4G1 specifically binds to full length-TrpRS (FIG. 17C).

Figure 18A:
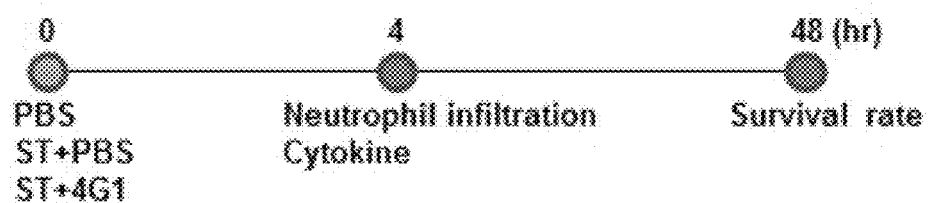
FIG. 18A-C shows a schematic diagram of an animal experiment using an antibody; the effect of the antibody on the expression of TNF-α and MIP-1α and the effect on the number of Ly6G$^+$ neutrophils.

Example 4-2. Decreased Secretion of TNF-α and MIP1-α by TrpRS-Specific Antibodies To examine the effect of the scFV 4G1 prepared in Example 5-1 on the innate immune response in the body, an animal experiment using mice was carried out according to the experimental outline of FIG. 18A.

Figure 18B:
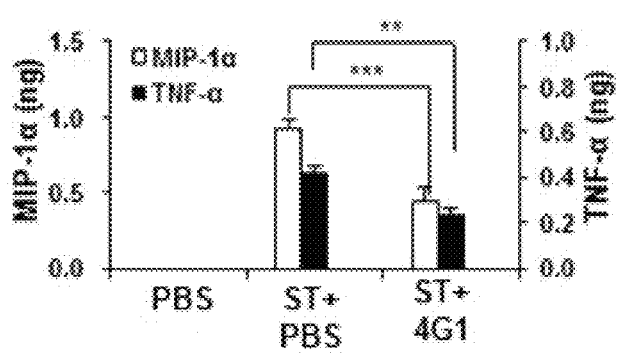
Figure 18C:
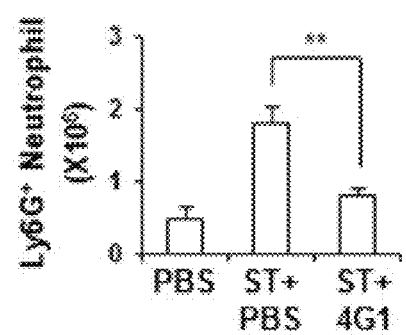

Mice were injected with PBS or scFv 4G1 in infected or uninfected groups by intraperitoneal injection of S. typhimurium. Four hours after the infection, the peritoneal fluid was extracted, and the number of Ly6G$^+$ cells was measured by flow cytometry. The amount of MIP-1a and TNF-α was analyzed by ELISA. The statistical significance of the comparison between the PBS-treated negative control and the results of each experimental condition was verified by one-way Anova test using GraphPad (ver. 4.0) software.* $p<0.001$,  $p<0.01$ ELISA analysis showed that the amount of MIP-1 alpha and TNF-α decreased in scFv 4G1-treated mice (FIG. 18B). In addition, flow cytometry analysis showed that Ly6G$^+$ macrophages decreased in scFv 4G1-treated mice (FIG. 18C).

Example 4-3. Effect of TrpRS-Specific Antibodies on Survival of Bacterially Infected Mice To confirm the effect of the scFv 4G1 prepared in Example 5-1 on the survival rate of the mice, an animal experiment using a mouse was conducted according to the experimental outline of FIG. 18A, and survival analysis was performed. As described above, mice were injected with PBS or scFv 4G1 in infected or uninfected groups by injecting S. typhimurium into the abdominal cavity. The survival rate of mice was 12, 24, 36, 48 hours after infection.

Figure 19:
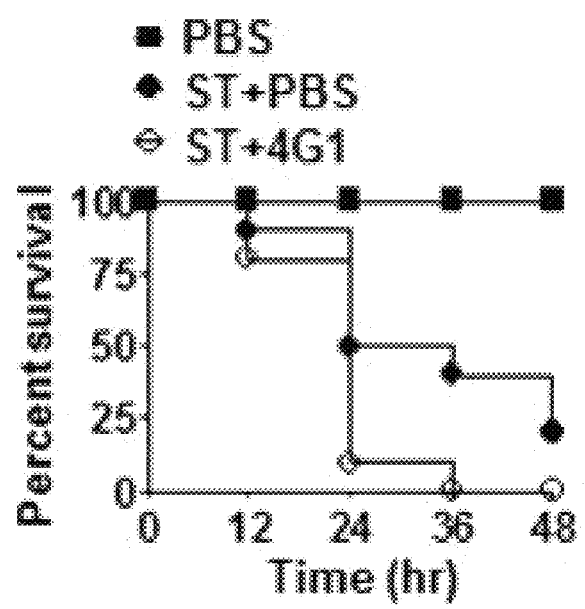
FIG. 19 shows a survival plot showing the effect of antibodies specific to TrpRS on the survival rate of *S. typhimurium*-infected mice.

As a result, in the control, ST+PBS (injection of PBS after infection with S. typhimurium) survival rate was 50% at 24 hours and 25% at 48 hours, but in ST+4G1 (scFv 4G1 injection after S. typhimurium infection) survival rate was less than 25%, and 0% at 36 hours. Thus, it was confirmed that the survival rate of mice was decreased in the group injected with scFv 4G1 (FIG. 19).

Example 5

Figure 20:
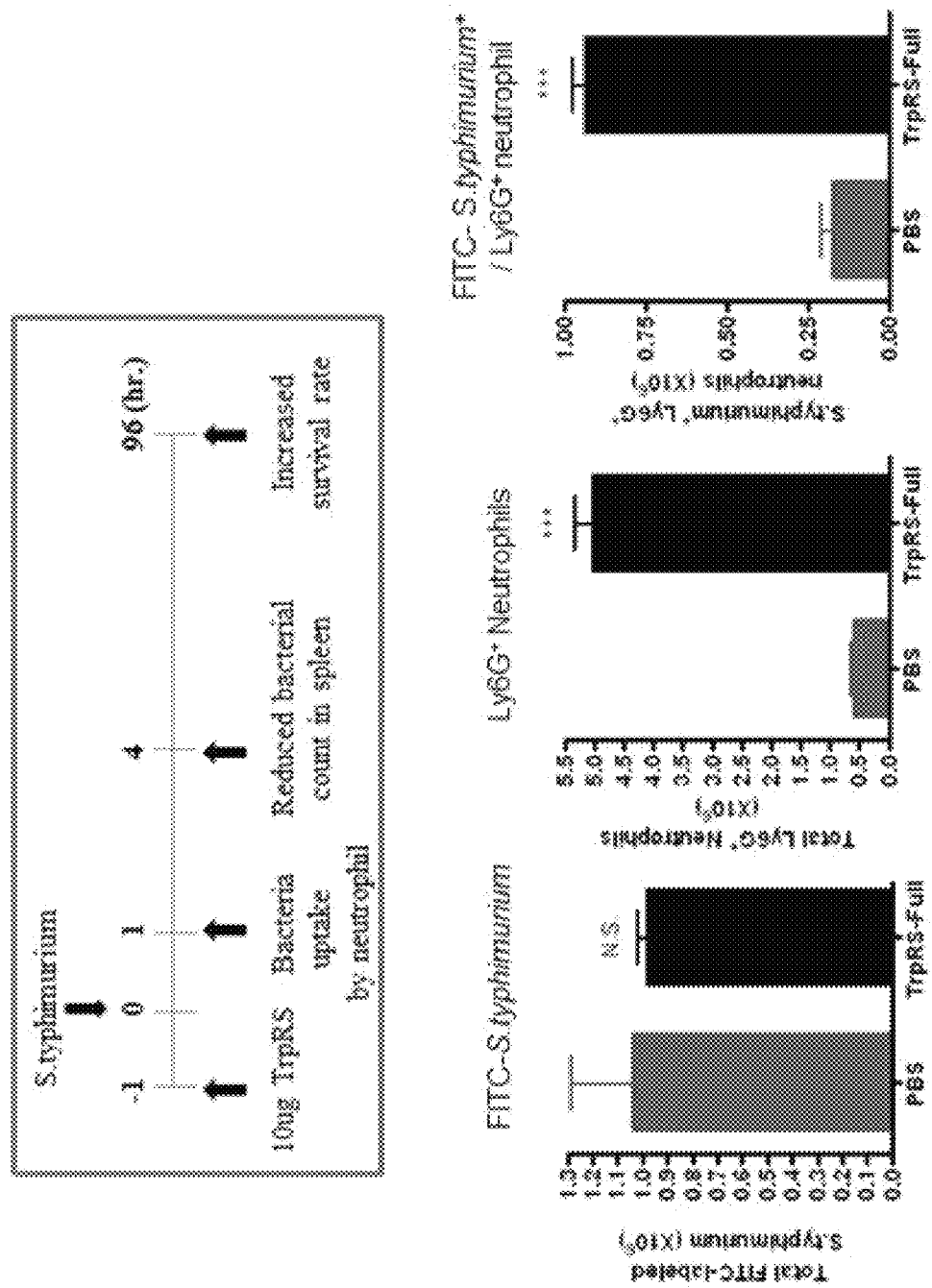
FIG. 20 shows the overviews of animal experiments to investigate the effect of TrpRS on the survival rate of mice infected with *S. typhimurium* (top in FIG. 20) and the results of flow cytometry showing the effect of TrpRS on the degree of *S. typhimurium*-adsorption or -absorption in infiltrating neutrophils.

Effect of TrpRS In Vivo Infection Inhibition and Increased Survival Rate after Infection Example 5-1. Effect of TrpRS on the Absorption of Infecting Bacteria by Invasive Neutrophils To investigate the effect of TrpRS on the survival rate of mice infected with S. typhimurium, an animal experiment using mice was carried out according to the outline of the experiment of FIG. 20 (FIG. 20, top), and the amount of S. typhimurium absorbed by and adsorbed onto infiltrated neutrophil was confirmed for one hour after infection (FIG. 20, bottom).

PBS or TrpRS (10 μg, 0.5 mg/kg) was injected intraperitoneally into mice (C57BL/6 mouse, 9-12 week old female) and fluorescently labeled S. typhimurium (FITC-labeled S. Typhimurium, $1×10^7$ CFU/mouse, 5~6 per group) was injected into the abdominal cavity 1 hour later. One hour after infection, mice were sacrificed and the peritoneal cells were separated and stained with Ly6G, Ly6C antibody and analyzed by flow cytometry. Statistical significance was verified by t-test. *** $p<0.001$ As a result, it was confirmed that the number of infiltrating neutrophils (Ly6G$^+$ Neutrophils) was also significantly increased in the full-length TrpRS-treated group (TrpRS-Full) compared with the PBS-treated control group (PBS), and that S. typhimurium (FITC-S. typhimurium$^+$/Ly6G$^+$ neutrophil) adsorbed onto and absorbed by neutrophils was significantly increased.

Example 5-2. Effects of TrpRS on Bacterial Clearance in Spleen and Liver

Figure 21A:
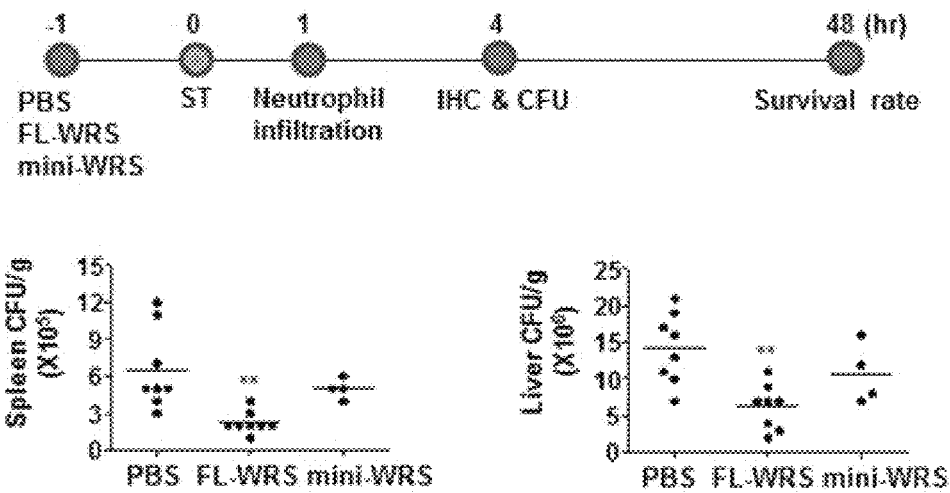
FIG. 21A-B shows a schematic diagram of animal experiments and shows the results of measuring IHC and CFU in the liver and spleen of mice, which were administered intraperitoneally with PBS(Con), FL-WRS, or mini-WRS (each 20 mg/mouse) 1 hour before the infection with *S. typhimurium* or *L. monocytogenes*.
Figure 21B:
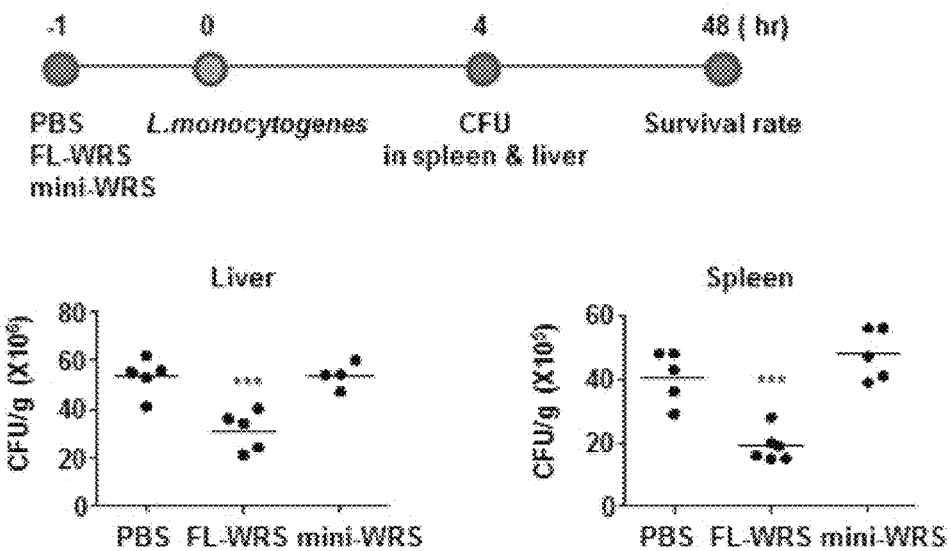

An animal experiment using a mouse was performed according to the outline of FIG. 15, and the degree of bacterial clearance of the spleen after 4 hours of infection was observed (FIG. 21). After 4 hours of infection with S. typhimurim (FIG. 21A) or L. monocytogenes (FIG. 21B), mice were sacrificed. Spleen and hepatic homogenate were made and cultured in NB agar medium (serial ratios of 4 to 8 mice per group) by 10× serial dilution. After culturing at 37° C. for 24 hours, the bacterial CFU was calculated and analyzed. Statistical significance was then verified by t-test using GraphPad (ver. 4.0) software. ** $p<0.01$ As a result, it was confirmed that, in S. typhimurium—infected mice, bacterial CFU in the spleen and liver of the group treated with full-length TrpRS was significantly reduced, compared with the group treated with mini-TrpRS (mini-WRS) or PBS (FIG. 21A). In mice infected with L. monocytogenes, the bacterial CFU in the spleen and liver of the group treated with full length-TrpRS (FL-WRS) was significantly lower than that of the group treated with mini-TrpRS (mini-WRS) (FIG. 21B). This shows that in the spleen and liver of TrpRS treated mice, the bacteria were eliminated before they caused cell infections.

Example 5-3. Effect of TrpRS on the Survival Rate of Bacteria-Infected Mice

Figure 22A:
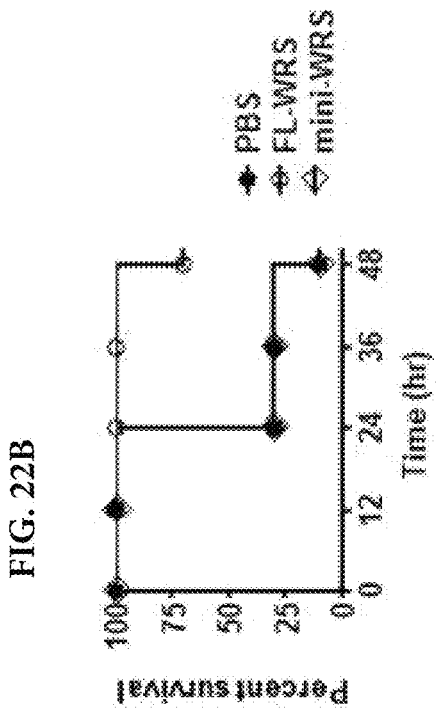
FIG. 22A-B shows a survival plot showing the effect of TrpRS on the survival rate of *S. typhimurium*-infected mice.
Figure 22B:
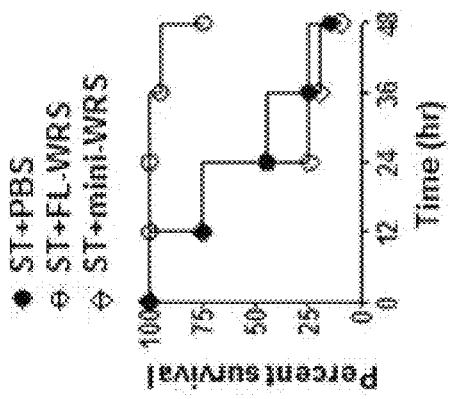

To investigate the effect of TrpRS on the survival rate of mice infected with S. typhimurim (FIG. 22A) or L. monocytogenes (FIG. 22B), animal experiments with mice were carried out according to the experimental outline of FIG. 21 (FIG. 22). Mice were injected with PBS, full-length TrpRS (FL-WRS) or mini-TrpRS (mini-WRS), followed by infusion of $1×10^7$ CFU S. typhimurium or L. monocytogenes into the peritoneal cavity. The survival rate of the mice at 12, 24, 36 and 48 hours after the infection was expressed as a survival plot according to the treatment conditions.

As a result, *S. typhimurim*-infected mice that were given full length-TrpRS were 100% viable until 36 hours post-infection and 75% survived until 48 hours post-infection, whereas the mice receiving PBS or mini-TrpRS were found to have over 80% mortality at 48 hours post-infection (FIG. 22A). *L. monocytogenes*-infected mice that received full length-TrpRS also survived 100% until 48 h before infection and 75% survived at 48 h after infection, whereas 75% of the mice receiving PBS or mini-TrpRS died in 24 hours (FIG. 22B). This indicates that the survival time of the TrpRS injected group was significantly longer than that of the control group or the mini-TrpRS treated group by the single injection of TrpRS alone.

The results of the above Examples show that full-length TrpRS lowers the mortality of bacteria-infected mice by activating innate immune responses.

INDUSTRIAL AVAILABILITY

As described above, the composition of the present invention can be effectively used to prevent diseases of humans and animals caused by bacterial, viral or fungal infection by inhibiting bacterial, viral or fungal infection at an early stage, particularly through activating innate immune response. In addition, the composition of the present invention can be used for immune enhancement and is highly industrially applicable.

What is claimed is:

1. A method for ameliorating or treating an infectious inflammatory disease caused by a bacterium, viruses or fungi in a subject in need thereof, the method comprising administering to the subject in need thereof a composition comprising a tryptophanyl-tRNA synthetase selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8 as an active ingredient in an amount effective for ameliorating or treating an infectious inflammatory disease caused by a bacterium, viruses or fungi, wherein the tryptophanyl-tRNA synthetase increases infiltration of neutrophils in the subject.

2. A method for immune enhancement in a subject in need thereof, the method comprising administering to the subject in need thereof a composition comprising a tryptophanyl-tRNA synthetase selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8 as an active ingredient in an amount effective for immune enhancement, wherein the tryptophanyl-tRNA synthetase increases infiltration of neutrophils in the subject.

3. The method of claim 1, wherein the composition is a pharmaceutical, food, or veterinary composition.

4. The method of claim 1, wherein the infectious inflammatory disease is selected from the group consisting of salmonellosis, food poisoning, typhoid, paratyphoid, sepsis, septic shock, systemic inflammatory response syndrome (SIRS), multiple organ dysfunction syndrome (MODS), pneumonia, pulmonary tuberculosis, tuberculosis, cold, influenza, airway infection, rhinitis, nasopharyngitis, otitis media, bronchitis, lymphadenitis, mumps, adenolymphitis, cheilitis, stomatitis, arthritis, myositis, dermatitis, vasculitis, gingivitis, pericementitis, keratitis, conjunctivitis, wound infection, peritonitis, hepatitis, osteomyelitis, cellulitis, meningitis, encephalitis, brain abscess, encephalomyelitis, cerebral meningitis, osteomyelitis, nephritis, carditis, endocarditis, enteritis, gastritis, esophagitis, duodenitis, colitis, urinary tract infection, cystitis, vaginitis, cervicitis, salpingitis, infectious erythema, bacterial dysentery, abscess and ulcer, bacteremia, diarrhea, dysentery, gastritis, gastroenteritis, genitourinary abscess, open wound or wound infection, purulent inflammation, abscesses, boils, pyoderma, impetigo, folliculitis, cellulitis, wound infection after surgery, scalded skin syndrome, skin burn syndrome, thrombotic thrombocytopenia, hemolytic uremic syndrome, renal failure, pyelonephritis, glomerulonephritis, nervous system abscess, otitis media, sinusitis, pharyngitis, tonsillitis, mastoiditis, soft tissue inflammation, dental infection, dacryocystitis, pleurisy, abdominal abscess, liver abscess, cholecystitis, spleen abscess, pericarditis, myocarditis, placentitis, amniotic fluid infection, mammitis, mastitis, puerperal fever, toxic shock syndrome, lyme disease, gas gangrene, atherosclerosis, mycobacterium avium syndrome (MAC), enterohaemorrhagic *Escherichia coli* (EHEC) infection, enteropathogenic *Escherichia coli* (EPEC) infection, enteroinvasive *Escherichia coli* (EIEC) infection, methicillin-resistant *Staphylococcus aureus* (MRSA) infections, vancomycin-resistant *Staphylococcus aureus* (VRSA) infections and listerosis.

5. The method of claim 2, wherein the composition is a pharmaceutical, food, or veterinary composition.

* * * * *

SEQUENCE LISTING

```
<160> NUMBER OF SEQ ID NOS: 18

<210> SEQ ID NO 1
<211> LENGTH: 471
<212> TYPE: PRT
<213> ORGANISM: Homo sapiens
<300> PUBLICATION INFORMATION:
<308> DATABASE ACCESSION NUMBER: NP_004175.2, NCBI Gene Database

<400> SEQUENCE: 1

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
        195                 200                 205

Asp Gln Ala Tyr Ser Tyr Ala Val Glu Asn Ala Lys Asp Ile Ile Ala
    210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
```

```
           260                 265                 270
Asp Cys Ile Gly Lys Ile Ser Phe Pro Ala Ile Gln Ala Ala Pro Ser
            275                 280                 285
Phe Ser Asn Ser Phe Pro Gln Ile Phe Arg Asp Arg Thr Asp Ile Gln
            290                 295                 300
Cys Leu Ile Pro Cys Ala Ile Asp Gln Asp Pro Tyr Phe Arg Met Thr
305                 310                 315                 320
Arg Asp Val Ala Pro Arg Ile Gly Tyr Pro Lys Pro Ala Leu Leu His
                325                 330                 335
Ser Thr Phe Phe Pro Ala Leu Gln Gly Ala Gln Thr Lys Met Ser Ala
            340                 345                 350
Ser Asp Pro Asn Ser Ser Ile Phe Leu Thr Asp Thr Ala Lys Gln Ile
            355                 360                 365
Lys Thr Lys Val Asn Lys His Ala Phe Ser Gly Gly Arg Asp Thr Ile
            370                 375                 380
Glu Glu His Arg Gln Phe Gly Gly Asn Cys Asp Val Asp Val Ser Phe
385                 390                 395                 400
Met Tyr Leu Thr Phe Phe Leu Glu Asp Asp Asp Lys Leu Glu Gln Ile
                405                 410                 415
Arg Lys Asp Tyr Thr Ser Gly Ala Met Leu Thr Gly Glu Leu Lys Lys
                420                 425                 430
Ala Leu Ile Glu Val Leu Gln Pro Leu Ile Ala Glu His Gln Ala Arg
            435                 440                 445
Arg Lys Glu Val Thr Asp Glu Ile Val Lys Glu Phe Met Thr Pro Arg
            450                 455                 460
Lys Leu Ser Phe Asp Phe Gln
465                 470

<210> SEQ ID NO 2
<211> LENGTH: 481
<212> TYPE: PRT
<213> ORGANISM: Rattus norvegicus
<300> PUBLICATION INFORMATION:
<308> DATABASE ACCESSION NUMBER: Q6P7B0.2, NCBI Gene Database

<400> SEQUENCE: 2

Met Ala Asp Met Pro Ser Gly Glu Ser Cys Thr Ser Pro Leu Glu Leu
1               5                   10                  15
Phe Asn Ser Ile Ala Ala Gln Gly Glu Leu Val Arg Ser Leu Lys Ala
            20                  25                  30
Gly Asn Ala Pro Lys Asp Glu Ile Glu Ser Ala Val Lys Met Leu Leu
        35                  40                  45
Ser Leu Lys Met Asn Tyr Lys Thr Ala Met Gly Glu Glu Tyr Lys Ala
    50                  55                  60
Gly Cys Pro Pro Gly Asn Ser Thr Ala Gly Ser Asn Gly Asp Pro Asp
65                  70                  75                  80
Ala Thr Lys Ala Ser Glu Asp Phe Val Asp Pro Trp Thr Val Arg Thr
                85                  90                  95
Ser Ser Ala Lys Gly Ile Asp Tyr Asp Lys Leu Ile Val Gln Phe Gly
            100                 105                 110
Ser Ser Lys Ile Asp Lys Glu Leu Ile Asn Arg Ile Glu Arg Ala Thr
            115                 120                 125
Gly Gln Arg Pro His Arg Phe Leu Arg Arg Gly Ile Phe Phe Ser His
        130                 135                 140
Arg Asp Met Asn Gln Ile Leu Asp Ala Tyr Glu Asn Lys Lys Pro Phe
```

```
            145                 150                 155                 160
Tyr Leu Tyr Thr Gly Arg Gly Pro Ser Ser Glu Ala Met His Leu Gly
                165                 170                 175

His Leu Val Pro Phe Ile Phe Thr Lys Trp Leu Gln Asp Val Phe Asp
                180                 185                 190

Val Pro Leu Val Ile Gln Met Ser Asp Asp Glu Lys Tyr Leu Trp Lys
                195                 200                 205

Asp Leu Thr Leu Glu Gln Ala Tyr Ser Tyr Thr Val Glu Asn Ala Lys
            210                 215                 220

Asp Ile Ile Ala Cys Gly Phe Asp Val Asn Lys Thr Phe Ile Phe Ser
225                 230                 235                 240

Asp Leu Glu Tyr Met Gly Gln Ser Pro Gly Phe Tyr Lys Asn Val Val
                245                 250                 255

Lys Ile Gln Lys His Val Thr Phe Asn Gln Val Lys Gly Ile Phe Gly
                260                 265                 270

Phe Thr Asp Ser Asp Cys Ile Gly Lys Ile Ser Phe Pro Ala Val Gln
                275                 280                 285

Ala Ala Pro Ser Phe Ser Asn Ser Phe Pro Lys Ile Phe Arg Asp Arg
        290                 295                 300

Thr Asp Ile Gln Cys Leu Ile Pro Cys Ala Ile Asp Gln Asp Pro Tyr
305                 310                 315                 320

Phe Arg Met Thr Arg Asp Val Ala Pro Arg Ile Gly His Pro Lys Pro
                325                 330                 335

Ala Leu Leu His Ser Thr Phe Phe Pro Ala Leu Gln Gly Ala Gln Thr
                340                 345                 350

Lys Met Ser Ala Ser Asp Pro Asn Ser Ser Ile Phe Leu Thr Asp Thr
            355                 360                 365

Ala Lys Gln Ile Lys Ser Lys Val Asn Lys His Ala Phe Ser Gly Gly
                370                 375                 380

Arg Asp Thr Val Glu Glu His Arg Gln Phe Gly Gly Asn Cys Glu Val
385                 390                 395                 400

Asp Val Ser Phe Met Tyr Leu Thr Phe Phe Leu Glu Asp Asp Asp Ser
                405                 410                 415

Leu Glu Gln Ile Arg Lys Asp Tyr Thr Ser Gly Ala Met Leu Thr Gly
                420                 425                 430

Glu Leu Lys Lys Thr Leu Ile Asp Val Leu Gln Pro Leu Ile Ala Glu
            435                 440                 445

His Gln Ala Arg Arg Lys Ala Val Thr Glu Thr Val Lys Glu Phe
            450                 455                 460

Met Ala Pro Arg Gln Leu Ser Phe His Phe Gln Cys Phe Cys Phe Asp
465                 470                 475                 480

Thr

<210> SEQ ID NO 3
<211> LENGTH: 481
<212> TYPE: PRT
<213> ORGANISM: Mus musculus
<300> PUBLICATION INFORMATION:
<308> DATABASE ACCESSION NUMBER: P32921.2, NCBI Gene Database

<400> SEQUENCE: 3

Met Ala Asp Met Pro Ser Gly Glu Ser Cys Thr Ser Pro Leu Glu Leu
1               5                   10                  15

Phe Asn Ser Ile Ala Thr Gln Gly Glu Leu Val Arg Ser Leu Lys Ala
            20                  25                  30
```

```
Gly Asn Ala Pro Lys Asp Glu Ile Asp Ser Ala Val Lys Met Leu Leu
            35                  40                  45

Ser Leu Lys Met Ser Tyr Lys Ala Ala Met Gly Glu Glu Tyr Lys Ala
 50                  55                  60

Gly Cys Pro Pro Gly Asn Pro Thr Ala Gly Arg Asn Cys Asp Ser Asp
 65                  70                  75                  80

Ala Thr Lys Ala Ser Glu Asp Phe Val Asp Pro Trp Thr Val Arg Thr
                 85                  90                  95

Ser Ser Ala Lys Gly Ile Asp Tyr Asp Lys Leu Ile Val Gln Phe Gly
            100                 105                 110

Ser Ser Lys Ile Asp Lys Glu Leu Ile Asn Arg Ile Glu Arg Ala Thr
            115                 120                 125

Gly Gln Arg Pro His Arg Phe Leu Arg Arg Gly Ile Phe Phe Ser His
130                 135                 140

Arg Asp Met Asn Gln Ile Leu Asp Ala Tyr Glu Asn Lys Lys Pro Phe
145                 150                 155                 160

Tyr Leu Tyr Thr Gly Arg Gly Pro Ser Ser Glu Ala Met His Leu Gly
                165                 170                 175

His Leu Val Pro Phe Ile Phe Thr Lys Trp Leu Gln Asp Val Phe Asn
            180                 185                 190

Val Pro Leu Val Ile Gln Met Ser Asp Asp Glu Lys Tyr Leu Trp Lys
            195                 200                 205

Asp Leu Thr Leu Glu Gln Ala Tyr Ser Tyr Thr Val Glu Asn Ala Lys
            210                 215                 220

Asp Ile Ile Ala Cys Gly Phe Asp Ile Asn Lys Thr Phe Ile Phe Ser
225                 230                 235                 240

Asp Leu Glu Tyr Met Gly Gln Ser Pro Gly Phe Tyr Arg Asn Val Val
                245                 250                 255

Lys Ile Gln Lys His Val Thr Phe Asn Gln Val Lys Gly Ile Phe Gly
            260                 265                 270

Phe Thr Asp Ser Asp Cys Ile Gly Lys Ile Ser Phe Pro Ala Val Gln
            275                 280                 285

Ala Ala Pro Ser Phe Ser Asn Ser Phe Pro Lys Ile Phe Arg Asp Arg
290                 295                 300

Thr Asp Ile Gln Cys Leu Ile Pro Cys Ala Ile Asp Gln Asp Pro Tyr
305                 310                 315                 320

Phe Arg Met Thr Arg Asp Val Ala Pro Arg Ile Gly His Pro Lys Pro
                325                 330                 335

Ala Leu Leu His Ser Thr Phe Phe Pro Ala Leu Gln Gly Ala Gln Thr
            340                 345                 350

Lys Met Ser Ala Ser Asp Pro Asn Ser Ser Ile Phe Leu Thr Asp Thr
            355                 360                 365

Ala Lys Gln Ile Lys Ser Lys Val Asn Lys His Ala Phe Ser Gly Gly
370                 375                 380

Arg Asp Thr Val Glu Glu His Arg Gln Phe Gly Gly Asn Cys Glu Val
385                 390                 395                 400

Asp Val Ser Phe Met Tyr Leu Thr Phe Phe Leu Glu Asp Asp Asp Arg
                405                 410                 415

Leu Glu Gln Ile Arg Lys Asp Tyr Thr Ser Gly Ala Met Leu Thr Gly
            420                 425                 430

Glu Leu Lys Lys Thr Leu Ile Asp Val Leu Gln Pro Leu Ile Ala Glu
            435                 440                 445
```

```
His Gln Ala Arg Arg Lys Ala Val Thr Glu Glu Thr Val Lys Glu Phe
    450                 455                 460
Met Thr Pro Arg Gln Leu Ser Phe His Phe Gln Cys Phe Cys Phe Asp
465                 470                 475                 480
Thr

<210> SEQ ID NO 4
<211> LENGTH: 476
<212> TYPE: PRT
<213> ORGANISM: Bos taurus
<300> PUBLICATION INFORMATION:
<308> DATABASE ACCESSION NUMBER: P17248.3, NCBI Gene Database

<400> SEQUENCE: 4

Met Ala Asp Met Ser Asn Gly Glu Gln Gly Cys Gly Ser Pro Leu Glu
1               5                   10                  15

Leu Phe His Ser Ile Ala Ala Gln Gly Glu Leu Val Arg Asp Leu Lys
            20                  25                  30

Ala Arg Asn Ala Ala Lys Asp Glu Ile Asp Ser Ala Val Lys Met Leu
        35                  40                  45

Leu Ser Leu Lys Thr Ser Tyr Lys Ala Ala Thr Gly Glu Asp Tyr Lys
50                  55                  60

Val Asp Cys Pro Pro Gly Asp Pro Ala Pro Glu Ser Gly Glu Gly Leu
65                  70                  75                  80

Asp Ala Thr Glu Ala Asp Glu Asp Phe Val Asp Pro Trp Thr Val Gln
                85                  90                  95

Thr Ser Ser Ala Lys Gly Ile Asp Tyr Asp Lys Leu Ile Val Arg Phe
            100                 105                 110

Gly Ser Ser Lys Ile Asp Lys Glu Leu Val Asn Arg Ile Glu Arg Ala
        115                 120                 125

Thr Gly Gln Arg Pro His Arg Phe Leu Arg Arg Gly Ile Phe Phe Ser
130                 135                 140

His Arg Asp Met His Gln Ile Leu Asp Ala Tyr Glu Asn Lys Lys Pro
145                 150                 155                 160

Phe Tyr Leu Tyr Thr Gly Arg Gly Pro Ser Ser Glu Ala Met His Val
                165                 170                 175

Gly His Leu Ile Pro Phe Ile Phe Thr Lys Trp Leu Gln Asp Val Phe
            180                 185                 190

Asn Val Pro Leu Val Ile Gln Met Thr Asp Asp Glu Lys Tyr Leu Trp
        195                 200                 205

Lys Asp Leu Thr Leu Asp Gln Ala Tyr Gly Tyr Ala Val Glu Asn Ala
210                 215                 220

Lys Asp Ile Ile Ala Cys Gly Phe Asp Ile Asn Lys Thr Phe Ile Phe
225                 230                 235                 240

Ser Asp Leu Asp Tyr Met Gly Met Ser Pro Gly Phe Tyr Lys Asn Val
                245                 250                 255

Val Lys Ile Gln Lys His Val Thr Phe Asn Gln Val Lys Gly Ile Phe
            260                 265                 270

Gly Phe Thr Asp Ser Asp Cys Ile Gly Lys Ile Ser Phe Pro Ala Ile
        275                 280                 285

Gln Ala Ala Pro Ser Phe Ser Asn Ser Phe Pro Gln Ile Phe Arg Asp
290                 295                 300

Arg Thr Asp Val Gln Cys Leu Ile Pro Cys Ala Ile Asp Gln Asp Pro
305                 310                 315                 320

Tyr Phe Arg Met Thr Arg Asp Val Ala Pro Arg Ile Gly Tyr Pro Lys
```

325                 330                 335
Pro Ala Leu Leu His Ser Thr Phe Phe Pro Ala Leu Gln Gly Ala Gln
            340                 345                 350
Thr Lys Met Ser Ala Ser Asp Pro Asn Ser Ser Ile Phe Leu Thr Asp
        355                 360                 365
Thr Ala Lys Gln Ile Lys Thr Lys Val Asn Lys His Ala Phe Ser Gly
    370                 375                 380
Gly Arg Asp Thr Val Glu Glu His Arg Gln Phe Gly Gly Asn Cys Asp
385                 390                 395                 400
Val Asp Val Ser Phe Met Tyr Leu Thr Phe Phe Leu Glu Asp Asp Asp
                405                 410                 415
Lys Leu Glu Gln Ile Arg Arg Asp Tyr Thr Ser Gly Ala Met Leu Thr
            420                 425                 430
Gly Glu Leu Lys Lys Glu Leu Ile Glu Val Leu Gln Pro Leu Ile Ala
        435                 440                 445
Glu His Gln Ala Arg Arg Lys Glu Val Thr Asp Glu Ile Val Lys Glu
    450                 455                 460
Phe Met Thr Pro Arg Lys Leu Ser Tyr Asp Phe Gln
465                 470                 475

<210> SEQ ID NO 5
<211> LENGTH: 476
<212> TYPE: PRT
<213> ORGANISM: Sus scrofa
<300> PUBLICATION INFORMATION:
<308> DATABASE ACCESSION NUMBER: JAA53775.1, NCBI Gene Database

<400> SEQUENCE: 5

Met Ala Asp Val Pro Asn Gly Glu Gln Gly Cys Ser Ser Pro Leu Glu
1               5                   10                  15
Leu Phe Asn Ser Ile Ala Ala Gln Gly Glu Leu Val Arg Ser Leu Lys
            20                  25                  30
Ala Arg His Ala Ala Lys Asp Glu Ile Asp Ser Ala Val Lys Met Leu
        35                  40                  45
Leu Ser Leu Lys Met Ser Tyr Lys Ala Ala Met Gly Glu Asp Tyr Lys
    50                  55                  60
Ala Asp Cys Pro Pro Gly Asn Arg Ala Pro Gly Ile Asp Ser Gly Leu
65              70                  75                  80
Asp Ala Thr Glu Ala Gly Asp Asp Phe Val Asp Pro Trp Thr Val Gln
                85                  90                  95
Thr Ser Ser Ala Lys Gly Ile Asp Tyr Asp Lys Leu Ile Val Arg Phe
            100                 105                 110
Gly Ser Ser Lys Ile Asp Lys Glu Leu Ile Asp Arg Ile Glu Arg Ala
        115                 120                 125
Thr Gly Gln Arg Pro His Arg Phe Leu Arg Arg Gly Ile Phe Phe Ser
    130                 135                 140
His Arg Asp Met Asn Gln Val Leu Asp Ala Tyr Glu Asn Lys Lys Pro
145                 150                 155                 160
Phe Tyr Leu Tyr Thr Gly Arg Gly Pro Ser Ser Glu Ala Met His Val
                165                 170                 175
Gly His Leu Ile Pro Phe Ile Phe Thr Lys Trp Leu Gln Asp Val Phe
            180                 185                 190
Asn Val Pro Leu Val Ile Gln Met Thr Asp Asp Glu Lys Tyr Leu Trp
        195                 200                 205
Lys Glu Leu Thr Leu Glu Gln Ala His Gly Tyr Ala Val Glu Asn Ala

```
            210                 215                 220
Lys Asp Ile Ile Ala Cys Gly Phe Asp Val Asn Lys Thr Phe Ile Phe
225                 230                 235                 240

Ser Asp Leu Asp Tyr Met Gly Met Ser Pro Gly Phe Tyr Lys Asn Val
                245                 250                 255

Val Lys Ile Gln Lys His Val Thr Phe Asn Gln Val Lys Gly Ile Phe
                260                 265                 270

Gly Phe Thr Asp Ser Asp Cys Ile Gly Lys Ile Ser Phe Pro Ala Ile
                275                 280                 285

Gln Ala Ala Pro Ser Phe Ser Ser Phe Pro Gln Ile Phe Arg Asp
290                 295                 300

Arg Thr Asp Ile Gln Cys Leu Ile Pro Cys Ala Ile Asp Gln Asp Pro
305                 310                 315                 320

Tyr Phe Arg Met Thr Arg Asp Val Ala Pro Arg Ile Gly Tyr Pro Lys
                325                 330                 335

Pro Ala Leu Leu His Ser Thr Phe Phe Pro Ala Leu Gln Gly Ala Gln
                340                 345                 350

Thr Lys Met Ser Ala Ser Asp Pro Asn Ser Ser Ile Phe Leu Thr Asp
                355                 360                 365

Thr Ala Lys Gln Ile Lys Thr Lys Val Asn Lys His Ala Phe Ser Gly
370                 375                 380

Gly Arg Asp Thr Ile Glu Glu His Arg Gln Phe Gly Gly Asn Cys Asp
385                 390                 395                 400

Val Asp Val Ser Phe Met Tyr Leu Thr Phe Phe Leu Glu Asp Asp Asp
                405                 410                 415

Arg Leu Glu Gln Ile Arg Lys Asp Tyr Ser Ser Gly Ala Met Leu Thr
                420                 425                 430

Gly Glu Leu Lys Lys Val Leu Ile Glu Val Leu Gln Pro Leu Ile Ala
                435                 440                 445

Glu His Gln Ala Arg Arg Lys Glu Val Thr Asp Glu Val Val Lys Glu
                450                 455                 460

Phe Met Thr Pro Arg Lys Leu Ser Tyr Asp Phe Glu
465                 470                 475

<210> SEQ ID NO 6
<211> LENGTH: 476
<212> TYPE: PRT
<213> ORGANISM: Ovis aries
<300> PUBLICATION INFORMATION:
<308> DATABASE ACCESSION NUMBER: XP_004018038.1, NCBI Gene Database

<400> SEQUENCE: 6

Met Ala Asp Met Pro Asn Gly Glu Gln Gly Tyr Gly Ser Pro Leu Glu
1               5                   10                  15

Leu Phe His Ser Ile Ala Ala Gln Gly Glu Leu Val Arg Gly Leu Lys
                20                  25                  30

Ala Arg Asn Ala Ala Lys Asp Glu Ile Asp Ser Ala Val Lys Met Leu
            35                  40                  45

Leu Ser Leu Lys Thr Ser Tyr Lys Ala Ala Thr Gly Glu Asp Tyr Lys
        50                  55                  60

Gly Asp His Pro Pro Glu Asp Pro Ala Pro Glu Ser Gly Glu Gly Leu
65                  70                  75                  80

Asp Ala Thr Gly Ala Asp Glu Asp Phe Val Asp Pro Trp Thr Val Gln
                85                  90                  95

Thr Ser Ser Ala Lys Gly Ile Asp Tyr Asp Lys Leu Ile Val Arg Phe
```

```
            100                 105                 110
Gly Ser Ser Lys Ile Asp Lys Glu Leu Val Asn Arg Ile Glu Arg Ala
        115                 120                 125

Thr Gly Gln Arg Pro His Arg Phe Leu Arg Gly Ile Phe Phe Ser
130                 135                 140

His Arg Asp Met His Gln Ile Leu Asp Ala Tyr Glu Asn Lys Lys Pro
145                 150                 155                 160

Phe Tyr Leu Tyr Thr Gly Arg Gly Pro Ser Ser Glu Ala Met His Val
                165                 170                 175

Gly His Leu Ile Pro Phe Ile Phe Thr Lys Trp Leu Gln Asp Val Phe
            180                 185                 190

Asn Val Pro Leu Val Ile Gln Met Thr Asp Asp Glu Lys Tyr Leu Trp
        195                 200                 205

Lys Asp Leu Thr Leu Asp Gln Ala Tyr Gly Tyr Ala Val Glu Asn Ala
    210                 215                 220

Lys Asp Ile Ile Ala Cys Gly Phe Asp Ile Asn Lys Thr Phe Ile Phe
225                 230                 235                 240

Ser Asp Leu Asp Tyr Met Gly Met Ser Pro Gly Phe Tyr Lys Asn Val
                245                 250                 255

Val Lys Ile Gln Lys His Val Thr Phe Asn Gln Val Lys Gly Ile Phe
            260                 265                 270

Gly Phe Thr Asp Ser Asp Cys Ile Gly Lys Ile Ser Phe Pro Ala Ile
        275                 280                 285

Gln Ala Ala Pro Ser Phe Ser Asn Ser Phe Pro Gln Ile Phe Arg Asp
    290                 295                 300

Arg Thr Asp Val Gln Cys Leu Ile Pro Cys Ala Ile Asp Gln Asp Pro
305                 310                 315                 320

Tyr Phe Arg Met Thr Arg Asp Val Ala Pro Arg Ile Gly Tyr Pro Lys
                325                 330                 335

Pro Ala Leu Leu His Ser Thr Phe Phe Pro Ala Leu Gln Gly Ala Gln
            340                 345                 350

Thr Lys Met Ser Ala Ser Asp Pro Asn Ser Ser Ile Phe Leu Thr Asp
        355                 360                 365

Thr Ala Lys Gln Ile Lys Thr Lys Val Asn Lys His Ala Phe Ser Gly
    370                 375                 380

Gly Arg Asp Thr Ile Glu Glu His Arg Gln Leu Gly Gly Asn Cys Asp
385                 390                 395                 400

Val Asp Val Ser Phe Met Tyr Leu Thr Phe Phe Leu Glu Asp Asp Asp
                405                 410                 415

Arg Leu Glu Gln Ile Arg Lys Asp Tyr Thr Ser Gly Ala Met Leu Thr
            420                 425                 430

Gly Glu Leu Lys Lys Glu Leu Ile Glu Val Leu Gln Pro Leu Ile Ala
        435                 440                 445

Glu His Gln Ala Arg Arg Lys Glu Val Thr Asp Glu Ile Val Lys Glu
    450                 455                 460

Phe Met Thr Pro Arg Lys Leu Ser Tyr Asp Phe Gln
465                 470                 475
```

<210> SEQ ID NO 7
<211> LENGTH: 476
<212> TYPE: PRT
<213> ORGANISM: Canis lupus
<300> PUBLICATION INFORMATION:
<308> DATABASE ACCESSION NUMBER: XP_537554.1, NCBI Gene Database

```
<400> SEQUENCE: 7

Met Ala Asp Met Pro Asn Gly Glu Gln Gly Phe Ala Ser Pro Leu Glu
1               5                   10                  15

Leu Phe Asn Ser Ile Ala Ala Gln Gly Glu Leu Val Arg Ser Leu Lys
            20                  25                  30

Ala Gly Lys Ala Ser Lys Asp Glu Ile Asp Ser Ala Val Lys Leu Leu
        35                  40                  45

Leu Ser Leu Lys Met Ser Tyr Lys Ala Thr Val Gly Glu Glu Tyr Lys
    50                  55                  60

Ala Asp Cys Pro Pro Ala Arg Pro Ala Pro Glu Asn Ser Arg Gly Leu
65                  70                  75                  80

Asn Ala Ala Glu Ala Glu Asp Phe Val Asp Pro Trp Thr Val Gln
                85                  90                  95

Thr Ser Ser Ala Lys Gly Ile Asp Tyr Asp Lys Leu Ile Val Arg Phe
            100                 105                 110

Gly Ser Ser Lys Ile Asp Lys Glu Leu Val Asn Arg Ile Glu Arg Ala
        115                 120                 125

Thr Gly Gln Lys Pro His Arg Phe Leu Arg Arg Gly Ile Phe Phe Ser
    130                 135                 140

His Arg Asp Met Asn Gln Ile Leu Asp Ala Tyr Glu Asn Lys Lys Pro
145                 150                 155                 160

Phe Tyr Leu Tyr Thr Gly Arg Gly Pro Ser Ser Glu Ala Met His Val
                165                 170                 175

Gly His Leu Ile Pro Phe Ile Phe Thr Lys Trp Leu Gln Asp Val Phe
            180                 185                 190

Asn Val Pro Leu Val Ile Gln Met Thr Asp Asp Glu Lys Tyr Leu Trp
        195                 200                 205

Lys Asp Leu Thr Leu Asp Gln Ala Tyr Gly Tyr Ala Val Glu Asn Ala
    210                 215                 220

Lys Asp Ile Ile Ala Cys Gly Phe Asp Ile Lys Lys Thr Phe Ile Phe
225                 230                 235                 240

Ser Asp Leu Asp Tyr Met Gly Met Ser Pro Gly Phe Tyr Lys Asn Val
                245                 250                 255

Val Lys Ile Gln Lys His Val Thr Phe Asn Gln Val Lys Gly Ile Phe
            260                 265                 270

Gly Phe Thr Asp Ser Asp Ser Ile Gly Lys Ile Ser Phe Pro Ala Ile
        275                 280                 285

Gln Ala Ala Pro Ser Phe Ser Asn Ser Phe Pro Gln Ile Phe Arg Asp
    290                 295                 300

Arg Thr Asp Ile Gln Cys Leu Ile Pro Cys Ala Ile Asp Gln Asp Pro
305                 310                 315                 320

Tyr Phe Arg Met Thr Arg Asp Val Ala Pro Arg Ile Gly Tyr Pro Lys
                325                 330                 335

Pro Ala Leu Leu His Ser Thr Phe Phe Pro Ala Leu Gln Gly Ala Gln
            340                 345                 350

Thr Lys Met Ser Ala Ser Asp Pro Asn Ser Ser Ile Phe Leu Thr Asp
        355                 360                 365

Thr Ala Lys Gln Ile Lys Thr Lys Val Asn Lys His Ala Phe Ser Gly
    370                 375                 380

Gly Arg Asp Thr Ile Glu Glu His Arg Gln Phe Gly Gly Asn Cys Asp
385                 390                 395                 400

Val Asp Val Ser Phe Met Tyr Leu Thr Phe Phe Leu Glu Asp Asp
                405                 410                 415
```

Lys Leu Glu Gln Ile Arg Lys Asp Tyr Thr Ser Gly Asp Met Leu Thr
420 425 430

Gly Glu Leu Lys Lys Thr Leu Ile Glu Val Leu Gln Pro Leu Ile Ala
435 440 445

Glu His Gln Ala Arg Lys Glu Val Thr Asp Glu Ile Val Lys Glu
450 455 460

Phe Met Thr Pro Arg Lys Leu Ser Tyr Asp Phe Gln
465 470 475

<210> SEQ ID NO 8
<211> LENGTH: 476
<212> TYPE: PRT
<213> ORGANISM: Felis catus
<300> PUBLICATION INFORMATION:
<308> DATABASE ACCESSION NUMBER: XP_003988038.1, NCBI Gene Database

<400> SEQUENCE: 8

Met Ala Asp Val Pro Asn Gly Glu Gln Gly Cys Ala Ser Pro Leu Glu
1               5                   10                  15

Leu Phe Asn Arg Ile Ala Ala Gln Gly Glu Leu Val Arg Ser Leu Lys
                20                  25                  30

Ala Gly Lys Ala Pro Gln Asp Glu Ile Asp Ser Ala Val Gln Met Leu
            35                  40                  45

Leu Ser Leu Lys Met Ser Tyr Lys Ala Ala Met Gly Glu Asp Tyr Lys
50                  55                  60

Ala Asp Cys Pro Pro Gly Asn Pro Ala Pro Gly Asn Asn Ser Gly Leu
65                  70                  75                  80

Gly Ala Thr Glu Ala Glu Glu Asp Phe Val Asp Pro Trp Thr Val Gln
                85                  90                  95

Thr Ser Ser Ala Lys Gly Ile Asp Tyr Asp Lys Leu Ile Val Arg Phe
            100                 105                 110

Gly Ser Ser Lys Ile Asp Lys Glu Leu Val Asn Arg Ile Glu Arg Ala
        115                 120                 125

Ile Gly Gln Lys Pro His Arg Phe Leu Arg Arg Gly Ile Phe Phe Ser
130                 135                 140

His Arg Asp Met Asn Gln Ile Leu Asp Ala Tyr Glu Asn Lys Lys Pro
145                 150                 155                 160

Phe Tyr Leu Tyr Thr Gly Arg Gly Pro Ser Ser Glu Ala Met His Val
                165                 170                 175

Gly His Leu Ile Pro Phe Ile Phe Thr Lys Trp Leu Gln Asp Val Phe
            180                 185                 190

Asn Val Pro Leu Val Ile Gln Met Thr Asp Asp Glu Lys Tyr Leu Trp
        195                 200                 205

Lys Asp Leu Thr Leu Asp Gln Ala Tyr Gly Tyr Ala Val Glu Asn Ala
210                 215                 220

Lys Asp Ile Ile Ala Cys Gly Phe Asp Ile Asn Lys Thr Phe Ile Phe
225                 230                 235                 240

Ser Asp Leu Asp Tyr Met Gly Ala Ser Pro Gly Phe Tyr Lys Asn Val
                245                 250                 255

Val Lys Ile Gln Lys His Val Thr Phe Asn Gln Val Lys Gly Ile Phe
            260                 265                 270

Gly Phe Thr Asp Ser Asp Ser Ile Gly Lys Ile Ser Phe Pro Ala Ile
        275                 280                 285

Gln Ala Ala Pro Ser Phe Ser Asn Ser Phe Pro Gln Ile Phe Gly Asp
290                 295                 300

Lys Thr Asp Val Gln Cys Leu Ile Pro Cys Ala Ile Asp Gln Asp Pro
305                 310                 315                 320

Tyr Phe Arg Met Thr Arg Asp Val Ala Pro Arg Ile Gly Tyr Pro Lys
            325                 330                 335

Pro Ala Leu Leu His Ser Thr Phe Phe Pro Ala Leu Gln Gly Ala Gln
            340                 345                 350

Thr Lys Met Ser Ala Ser Asp Pro Asn Ser Ser Ile Phe Leu Thr Asp
        355                 360                 365

Thr Ala Lys Gln Ile Lys Thr Lys Val Asn Lys His Ala Phe Ser Gly
370                 375                 380

Gly Arg Asp Thr Val Glu Glu His Arg Glu Phe Gly Gly Asn Cys Asp
385                 390                 395                 400

Val Asp Val Ser Phe Met Tyr Leu Thr Phe Phe Leu Glu Asp Asp
                405                 410                 415

Arg Leu Glu Gln Ile Arg Lys Asp Tyr Thr Ser Gly Ala Met Leu Thr
            420                 425                 430

Gly Glu Leu Lys Lys Ile Leu Ile Glu Val Leu Gln Pro Leu Ile Ala
        435                 440                 445

Glu His Gln Ala Arg Arg Lys Glu Val Thr Asp Glu Ile Val Lys Glu
    450                 455                 460

Phe Met Thr Pro Arg Lys Leu Ser Tyr Asp Phe Gln
465                 470                 475

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      hTNF-alpha Forward primer

<400> SEQUENCE: 9
ggagaagggt gaccgactca                                             20

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      hTNF-alpha Reverse primer

<400> SEQUENCE: 10
ctgcccagac tcggcaa                                                17

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      hTrpRS Forward primer

<400> SEQUENCE: 11
aagaattcat gcccaacagt gagccc                                      26

<210> SEQ ID NO 12
<211> LENGTH: 32
<212> TYPE: DNA
<213> ORGANISM: Artificial Sequence
<220> FEATURE:

<223> OTHER INFORMATION: Description of Artificial Sequence: Synthetic
      hTrpRS Reverse primer

<400> SEQUENCE: 12
aactcgagct accctggagg acagtcagcc tt                                    32

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      GAPDH forward primer

<400> SEQUENCE: 13
cgctctctgc tcctcctgtt c                                                21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      GAPDH reverse primer

<400> SEQUENCE: 14
ttgactccga ccttcacctt cc                                               22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      hMIP-1 alpha Forward primer

<400> SEQUENCE: 15
accatggctc tctgcaacca                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      hMIP-1 alpha Reverse primer

<400> SEQUENCE: 16
ttaagaagag tcccacagtg                                                  20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      hMIP-1 beta Forward primer

```
<400> SEQUENCE: 17
agcctcacct ctgagaaaac c                                              21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      hMIP-1 beta Reverse primer

<400> SEQUENCE: 18
gcaacagcag agaaacagtg ac                                             22
```